US009718837B2

(12) United States Patent
Zhao et al.

(10) Patent No.: US 9,718,837 B2
(45) Date of Patent: Aug. 1, 2017

(54) NITROGEN-CONTAINING HETEROCYCLIC RING SUBSTITUTED DIHYDROARTEMISININ DERIVATIVES AND USE THEREOF

(71) Applicant: Shenyang Pharmaceutical University, Shenyang (CN)

(72) Inventors: Linxiang Zhao, Shenyang (CN); Dan Liu, Shenyang (CN); Hang Zhong, Shenyang (CN); Xuan Zhao, Shenyang (CN); Yongkui Jing, Shenyang (CN)

(73) Assignee: Shenyang Pharmaceutical University, Shenyang (CN)

( * ) Notice: Subject to any disclaimer, the term of this patent is extended or adjusted under 35 U.S.C. 154(b) by 0 days.

(21) Appl. No.: 14/769,079

(22) PCT Filed: Feb. 20, 2014

(86) PCT No.: PCT/CN2014/072301
§ 371 (c)(1),
(2) Date: Aug. 19, 2015

(87) PCT Pub. No.: WO2014/127722
PCT Pub. Date: Aug. 28, 2014

(65) Prior Publication Data
US 2016/0009729 A1   Jan. 14, 2016

(30) Foreign Application Priority Data

Feb. 20, 2013 (CN) .......................... 2013 1 0054304

(51) Int. Cl.
*C07D 493/18* (2006.01)
(52) U.S. Cl.
CPC ................. *C07D 493/18* (2013.01)
(58) Field of Classification Search
None
See application file for complete search history.

(56) References Cited

FOREIGN PATENT DOCUMENTS

| CN | 101580510 A | 11/2009 | |
|----|-------------|---------|---|
| CN | 103113386 A | 5/2013 | |
| GB | WO 03048167 A1 * | 6/2003 | ........... C07D 493/18 |
| WO | 01/04123 A2 | 1/2001 | |
| WO | 03/048167 A1 | 6/2003 | |

OTHER PUBLICATIONS

Yang, X.-L. et al Lett Drug Design & Discov, 2009, vol. 6, pp. 595-598.*
Yang, et al., "Design, Synthesis and Antiproliferative Activities of Artemisinin Derivatives Containing a Substituted Piperazine," *Letter in Drug Design & Discovery*, vol. 6, No. 8, pp. 595-598 (2009).
International Search Report from International Application No. PCT/CN2014/072301 dated May 26, 2014.

* cited by examiner

*Primary Examiner* — Heidi Reese
(74) *Attorney, Agent, or Firm* — Kilpatrick Townsend & Stockton LLP

(57) ABSTRACT

The present invention belongs to the field of medicinal technique, specifically relates to nitrogen-containing heterocyclic ring-substituted dihydroartemisinin derivatives and their optical isomers according to formula I or II; wherein substituent X, Y, R, $R_1$, $R_2$, $R_3$ and $R_4$ are as defined in the Description. The derivatives and compositions thereof can be prepared into clinically acceptable tablets, capsules, injections, ointments, etc., and thus have pharmaceutical uses in the treatment and/or prevention of cancers.

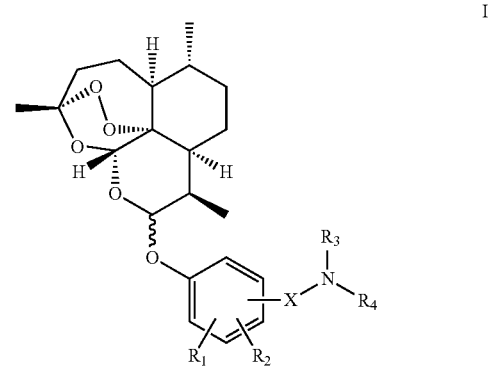

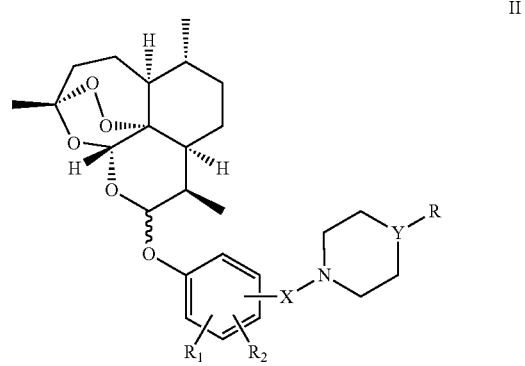

17 Claims, No Drawings

NITROGEN-CONTAINING HETEROCYCLIC RING SUBSTITUTED DIHYDROARTEMISININ DERIVATIVES AND USE THEREOF

CROSS-REFERENCE TO RELATED APPLICATIONS

This application is the U.S. National Stage entry of PCT/CN2014/072301, filed Feb. 20, 2014, which claims the benefit of Chinese Patent Application No. 201310054304.1, filed Feb. 20, 2013, the disclosures of each are herein incorporated by reference.

FIELD OF THE INVENTION

The present invention belongs to the field of medicinal technique. In particular, the invention relates to nitrogen-containing heterocyclic ring-substituted dihydroartemisinin derivatives, their optical isomers and preparation method thereof, pharmaceutical compositions comprising such derivatives as active ingredients, and uses in the preparation of a medicament for the treatment and/or prevention of various cancers.

BACKGROUND OF THE INVENTION

Cancers severely imperil health and life of human, which have become the second cause of death only except cardiovascular diseases (CVDs), lead to death beyond the sum of acquired immune deficiency syndrome (AIDS) and tuberculosis and malaria, and the incidence rate thereof increases yearly. It is expected that the number of cancer patients around the world would exceed 26 million, and the number of death thereof would reach 17 million in 2030. Nowadays, chemotherapy has been one of effective methods for the treatment of tumor. In recent years, the tumor chemotherapy has achieved remarkable progresses, prolonging cancer patients' survival time significantly, especially the breakthrough for the treatment of leukemia, malignant lymphoma and so forth. However, for solid tumors that account for more than 90% of malignant tumors and are harmful to human life and health seriously, the treatment does not achieve satisfactory results. Therefore, the research and development of new antitumor drugs have become an urgent need.

Artemisinin is a sesquiterpene lactone with a peroxide bridge structure, which is isolated from Chinese medicinal plant *Artemisia annua* L., and extensively used as an antimalarial drug. Then, the researchers modified artemisinin and obtained dihydroartemisinin, artesunate, artemether arteether, etc., all of which have a stronger resistance to malaria with fewer side effects. Studies in recent years have found that artemisinin and its derivatives also have other various pharmacological effects, such as anti-tumor antivirus, anti-inflammatory, immune regulation effects, etc. Among them, the studies on antitumor activity of artemisinin and its derivatives have received a widespread attention. Artemisinin and its derivatives have certain inhibitory or killing effect for variety of tumor cells, including leukemia, breast cancer, cervical cancer, ovarian cancer, stomach cancer, colon cancer, liver cancer, pancreatic cancer, lung cancer, osteosarcoma, etc., and almost have no influence on normal cells at a therapeutic concentration. Such mechanism for killing tumor cells is possibly by ways of inducing apoptosis in tumor cells, inhibiting proliferation of tumor cells and inhibiting tumor angiogenesis, reversing multi-drug resistance, and the like. At the same time, studies have found that artemisinin compounds have no cross-resistance with the traditional chemotherapy drugs, and can reverse the multi-drug, resistance of tumor cells. Artemisinin is interested by people, and thus has become a potential lead compound of new anti-cancer drugs with high efficacy and low toxicity.

In view of above, the present inventors have designed and synthesized a series of nitrogen-containing heterocyclic ring substituted dihydroartemisinin derivatives, and the results of antitumor activity in vitro screening tests have showed that such synthesized compounds have a good antitumor activity.

SUMMARY OF THE INVENTION

It is an object of the present invention to provide a series of nitrogen-containing heterocyclic ring substituted dihydroartemisinin derivatives, and to provide the use in antitumor drugs thereof.

The invention relates to the derivatives of formula I or II as defined below, and optical isomers thereof, and their clinically acceptable tablets, capsules, injections, ointments, etc.

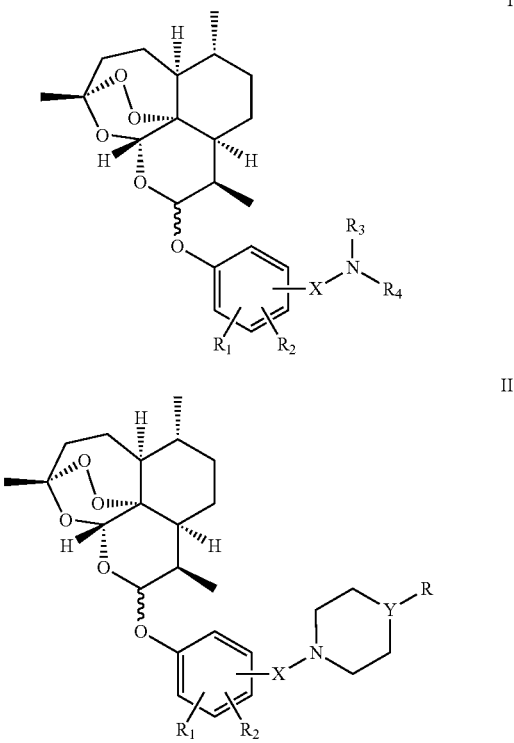

wherein

X is $-(CH_2)_n-$,

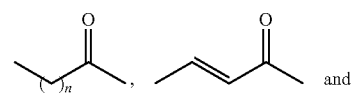

and

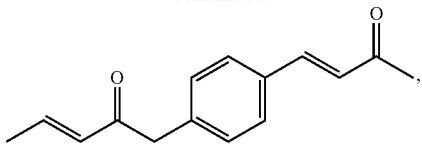

and n is independently an integer of from 1 to 3.

Y is CH, N or O.

$R_3$ and $R_4$, together with the nitrogen atom to which they attached, form a 5-membered saturated and unsaturated heterocyclic group, which may contain 0 to 2 heteroatoms selected from N, O and S, in addition to the nitrogen atom connected by $R_3$ and $R_4$, and may be optionally substituted with 1 to 3 same or different substituents selected from $R_5$.

R is hydrogen, $C_1$-$C_{10}$ alkyl, a heteroatom-containing $C_3$-$C_7$ cycloalkyl group s, Ar,

wherein Ar is phenyl optionally substituted with 1 to 5 same or different substituents selected from $R_6$, or 5- to 10-membered hetetoaryl optionally substituted with 1 to 5 same or different substituents selected from $R_7$, said heteroaryl may contain 1 to 3 heteroatoms selected from N, O and S.

$R_1$-$R_2$ and $R_5$-$R_7$ are independently selected from hydrogen, halogen, trifluoromethyl, trifluromethoxy, hydroxyl, carboxyl, nitro, cyano, ($C_1$-$C_4$) alkyl, ($C_1$-$C_4$) alkoxy, or other substituents.

Preferably, the present invention relates to the derivatives of general formula I, and optical isomers thereof, and their clinically acceptable tablets, capsules, injections, ointments, etc., wherein, X is —$(CH_2)_n$—,

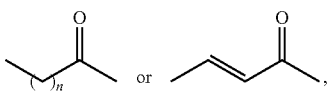

and n is independently an integer of from 1 to 3.

$R_3$ and $R_4$, together with the nitrogen atom to which they attached, form a 5-membered saturated and unsaturated heterocyclic group, which may contain 0 to 2 heteroatoms selected from N, O and S, in addition to the nitrogen atom connected by $R_5$ and $R_6$, and may be optionally substituted with 1 to 3 same or different substituents selected from $R_5$.

$R_5$ is independently selected from hydrogen, halogen, trifluoromethyl, trifluoromethoxy, hydroxyl, carboxyl, nitro, cyano, ($C_1$-$C_4$) alkyl, ($C_1$-$C_4$) alkoxy, or other substituents.

Preferably, the present invention relates to the derivatives of general formula II, and optical isomers thereof, and their clinically acceptable tablets, capsules, injections, ointments, etc., wherein, X is —$(CH_2)_n$—,

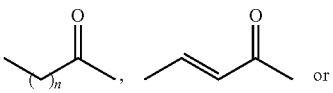

and n is independently an integer of from 1 to 3.

Y is CH, N or O.

R is hydrogen, $C_1$-$C_{10}$ alkyl, a heteroatom-containing $C_3$-$C_7$ cycloalkyl group, Ar,

wherein Ar is phenyl optionally substituted with 1 to 5 same or different substituents selected from $R_6$, 5- to 10-membered heteroaryl optionally substituted with 1 to 5 same or different substituents selected from $R_7$, said heteroaryl may contain 1 to 3 heteroatom selected from N, O and S.

$R_1$-$R_2$ and $R_6$-$R_7$ are independently selected from hydrogen, halogen, trifluoromethyl, trifluoromethoxy, hydroxyl, carboxyl, nitro, cyano, ($C_1$-$C_4$) alkyl, ($C_1$-$C_4$) alkoxy, or other substituents.

More preferably, the present invention relates to compounds of general formula I, and optical isomers thereof, and their clinically acceptable tablets, capsules, injections, ointments, etc, wherein: X is

$R_3$ and $R_4$, together with the nitrogen atom to which they attached, form a 5-membered saturated and unsaturated heterocyclic group; $R_1$-$R_2$ are optionally substituted.

More preferably, the present invention relates to compounds of general formula I, and optical isomers thereof, and their clinically acceptable tablets, capsules, injections, ointments, etc. wherein: X is

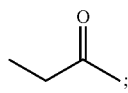

$R_3$ and $R_4$, together with the nitrogen atom to which they attached, form a 5-membered saturated and unsaturated heterocyclic group; $R_1$-$R_2$ are optionally substituted.

More preferably, the present invention relates to compounds of general formula II, and optical isomers thereof, and their clinically acceptable tablets, capsules, injections, ointments, etc., wherein: X, is

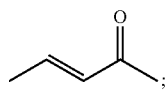

$R_3$ and $R_4$, together with the nitrogen atom to which they attached, form a 5-membered saturated and unsaturated heterocyclic group; $R_1$ and $R_2$ are optionally substituted.

More preferably, the present invention relates to compounds of general formula II, and optical isomers thereof, and their clinically acceptable tablets, capsules, injections, ointments, etc., wherein: X is

Y is CH; R is hydrogen or a heteroatom-containing $C_3$-$C_7$ cycloalkyl group; $R_1$ and $R_2$ are independently selected from hydrogen, halogen, trifluoromethyl, trifluoromethoxy, hydroxyl, carboxyl, nitro, cyano, ($C_1$-$C_4$) alkyl, ($C_1$-$C_4$) alkoxy, or other substituents.

More preferably, the present invention relates to compounds of general formula II, and optical isomers thereof, and their clinically acceptable tablet, capsules, injections, ointments, etc., wherein: X is

Y is N; R is hydrogen, $C_1$-$C_{10}$ alkyl, a heteroatom-containing $C_3$-$C_7$ cycloalkyl group, Ar,

wherein Ar is phenyl optionally substituted with 1 to 5 same or different substituents selected from $R_6$, 5- to 10-membered heteroaryl optionally substituted with 1 to 5 same or different substituents selected from $R_7$, said heteroaryl may contain 1 to 3 heteroatoms selected from N, O and S; $R_1$-$R_2$ and $R_6$-$R_7$ are independently selected from hydrogen, halogen, trifluoromethyl, trifluoromethoxy, hydroxyl, carboxyl, nitro, cyano, ($C_1$-$C_4$) alkyl, ($C_1$-$C_4$) alkoxy, or other substituents.

More preferably, the present invention relates to compounds of general formula II, and optical isomers thereof, and their clinically acceptable tablets, capsules, injections, ointments, etc., wherein: X is

Y is O; $R_1$ and $R_2$ are independently selected from hydrogen, halogen, trifluoromethyl, trifluoromethoxy, hydroxyl, carboxyl, nitro, cyano, ($C_1$-$C_4$) alkyl, ($C_1$-$C_4$) alkoxy, or other substituents.

More preferably, the present invention relates to compounds of general formula II, and optical isomers thereof, and their clinically acceptable tablets, capsules, injections, ointments, etc., wherein: X is

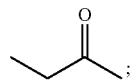

Y is CH; R is hydrogen or a heteroatom-containing $C_3$-$C_7$ cycloalkyl group; $R_1$ and $R_2$ are independently selected from hydrogen, halogen, trifluoromethyl, trifluoromethoxy, hydroxyl, carboxyl, nitro, cyano, ($C_1$-$C_4$) alkyl, ($C_1$-$C_4$) alkoxy, or other substituents.

More preferably, the present invention relates to the following compounds of general formula II, and optical isomers thereof, and their clinically acceptable tablets, capsules, injections, ointments, etc., wherein: X is

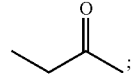

Y is N; R is hydrogen, $C_1$-$C_{10}$ alkyl, a heteroatom-containing $C_3$-$C_7$ cycloalkyl group, Ar,

wherein Ar is phenyl optionally substituted with 1 to 5 same or different substituents selected from $R_6$, 5- to 10-membered heteroaryl optionally substituted with 1 to 5 same or different substituents selected from $R_7$, said heteroaryl may contain 1 to 3 heteroatom selected from N, O and S; $R_1$-$R_2$ and $R_6$-$R_7$ are independently selected from hydrogen, halogen, trifluoromethyl, trifluoromethoxy, hydroxyl, carboxyl, nitro, cyano, ($C_1$-$C_4$) alkyl, ($C_1$-$C_4$) alkoxy, or other substituents.

More preferably, the present invention relates to compounds of general formula II, and optical isomers thereof, and their clinically acceptable tablets, capsules, injections, ointments, etc., wherein: X is

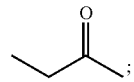

Y is O; $R_1$ and $R_2$ are independently selected from hydrogen, halogen, trifluoromethyl, trifluorormethoxy, hydroxyl, carboxyl, nitro, cyano, ($C_1$-$C_4$) alkyl, ($C_1$-$C_4$) alkoxy, or other substituents.

More preferably, the present invention relates to compounds of general formula II, and optical isomers thereof, and their clinically acceptable tablets, capsules, injections, ointments, etc., wherein: X is

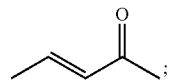

Y is CH; R is hydrogen or a heteroatom-containing $C_3$-$C_7$ cycloalkyl group; $R_1$-$R_2$ are independently selected from hydrogen, halogen, trifluoromethyl, trifluoromethoxy, hydroxyl, carboxyl, nitro, cyano, ($C_1$-$C_4$) alkyl, ($C_1$-$C_4$) alkoxy, or other substituents.

More preferably, the present invention relates to compounds of general formula II, and optical isomers thereof, and their clinically acceptable tablets, capsules, injections, ointments, etc., wherein: X is

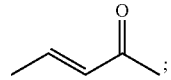

Y is N; R is hydrogen, $C_1$-$C_{10}$ alkyl, a heteroatom-containing $C_3$-$C_7$ cycloalkyl group, Ar,

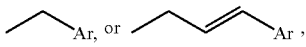

wherein Ar is phenyl optionally substituted with 1 to 5 same or different substituents selected from $R_6$, 5- to 10-membered heteroaryl optionally substituted with 1 to 5 same or different substituents selected from $R_7$, said heteroaryl may contain 1 to 3 heteroatom selected from N, O and S; $R_1$-$R_2$ and $R_6$-$R_7$ are independently selected from hydrogen, halogen, trifluoromethyl, trifluoromethoxy, hydroxyl, carboxyl, nitro, cyano, ($C_1$-$C_4$) alkyl, ($C_1$-$C_4$) alkoxy, or other substituents.

More preferably, the present invention relates to compounds of general formula II, and optical isomers thereof, and their clinically acceptable tablets, capsules, injections, ointments, etc., wherein: X is

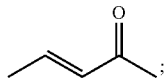

Y is O; $R_1$ and $R_2$ are independently selected from hydrogen, halogen, trifluoromethyl, trifluoromethoxy, hydroxyl, carboxyl, nitro, cyano, ($C_1$-$C_4$) alkyl, ($C_1$-$C_4$) alkoxy, or other substituents.

More preferably, the present invention relates to compounds of general formula II, and optical isomers thereof, and their clinically acceptable tablets, capsules, injections, ointments, etc., wherein: X is

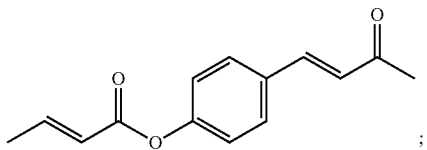

Y is N; R is hydrogen, $C_1$-$C_{10}$ alkyl, a heteroatom-containing $C_3$-$C_7$ cycloalkyl group, Ar,

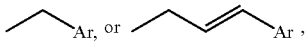

wherein Ar is phenyl optionally substituted with 1 to 5 same or different substituents selected from $R_6$, 5- to 10-membered heteroaryl optionally substituted with 1 to 5 same or different substituents selected from $R_7$, said heteroaryl may contain 1 to 3 heteroatom selected from N, O and S; $R_1$-$R_2$ and $R_6$-$R_7$ are independently selected from hydrogen, halogen, trifluoromethyl, trifluoromethoxy, hydroxyl, carboxyl, nitro, cyano, ($C_1$-$C_4$) alkyl, ($C_1$-$C_4$) alkoxy, or other substituents.

The compounds of present invention may exist in form of stereoisomers, including enantiomers and diastereomers. The present invention relates to enantiomers, diastereomers and their mixtures. The diastereomers may be separated from the racemic forms to the individual stereoisomeric form according to methods that are well known to those skilled in the art.

In addition, the invention also includes prodrugs of the present derivatives. According to the present invention, prodrugs are derivatives of general formula I or II, and they themselves may have weak or even no activity, but after administration, they are transformed into the corresponding bioactive forms under physiological conditions (for example, through metabolism, solvent decomposition or other means).

Unless otherwise indicated, as used herein, the term "halogen" refers to fluorine, chlorine, bromine or iodine; "alkyl" refers to straight or branched alkyl; "alkoxy" refers to straight or branched alkoxy.

The compounds of the present invention can have asymmetric centers, and therefore can exist in different enantiomeric or diastereomeric forms. The present invention relates to all the forms of the compounds of the present invention, i.e., optical isomers, racemates and mixtures thereof. "Racemate" refers to a mixture containing the same amount of a pair of enantiomers.

The present invention includes pharmaceutical compositions comprising the compounds according to the general formula I or II, or optically active forms thereof, and pharmaceutically acceptable excipients. The term "pharmaceutically acceptable excipient" refers to any drug diluents, adjuvant and/or carriers used in pharmaceutical field. The derivatives of the present invention can be used in combination with other active ingredients, as long as they do not have other adverse effects, such as allergic reactions.

Pharmaceutical compositions of this invention can be formulated into several dosage forms, containing some pharmaceutical excipients commonly used in the art, for example, oral formulations (such as tablets, capsules, solution or suspension), injectable formulations (such as injectable solution or suspension, or lyophilized powder that can be injected immediately before use by adding water); topical formulations (e.g., ointment or solution).

The carriers used in the pharmaceutical compositions of the present invention are common available types in the pharmaceutical field, including: adhesives, lubricants, disintegrating agents, cosolvents, diluents, stabilizers, suspending agents, pigment, flavoring agents, or the like used in oral formulations; preservatives, solubilizing agents, stabilizer, or the like used in injectable formulations; substrates, diluents, lubricants, preservatives, or the like used in local formulations. Pharmaceutical formulations may be administered orally or parenterally (for example, intravenously, subcutaneously, intraperitoneally or locally). If certain drugs are unstable under the stomach conditions, they can be made into coated tablets.

By in vitro activity screening and in vivo pharmacodynamic studies, we have found that the compounds of present invention have antitumor activity, and thus they can be used in the preparation of medicaments for treating and/or preventing cancers, such as breast, lung, colon, rectal, stomach, prostate, bladder, uterus, pancreatic and ovary cancers, etc.

The derivatives of the present invention, as active ingredients, are useful for preparing a medicament for the treatment and/or prevention of cancers. The present invention also provides a method for treating or preventing above-mentioned diseases, including administrating an therapeutically effective amount of the compounds of the present invention to patients who suffer from or are susceptible to the diseases. The clinic dosage of the derivatives of dihydroartemisinin of above formula I and II depends on various factors, such as the subject being treated, the specific administration route, and the severity of the disease, and the optimal dosage can be determined by the specific doctor who is responsible for the patient.

The active compounds of the invention may be used as the sole anticancer drug, or in combination with one or more other antitumor drugs. The combined treatment is achieved by administrating individual anticancer drugs concurrently, subsequently or separately.

The following Experimental Examples and Preparation Examples further illustrate and exemplify the compounds of the invention and the preparation methods thereof. It should be understood that the following Examples are given for the purposes of illustrating this invention and are not intended to limit the scope thereof in any way. In the following Examples unless otherwise stated, a compound having a chiral center exists as an individual enantiomer, and molecules could exist as a racemic mixture of diastereomers if no resolution process is performed. The individual enantiomer/diastereomer may be separated according to methods well known to those skilled in the art.

The following synthetic schemes describe the methods for preparing the derivatives of formula I or II of the invention. All raw materials can be prepared through the methods in the schemes or prepared by common techniques known to those skilled in the field of organic chemistry, or can be commercially purchased. All final derivatives of the invention are prepared by the following methods or similar ones known to those skilled in the field of organic chemistry. All variable factors employed in the schemes are as defined hereinafter or as defined in the claims.

Scheme 1

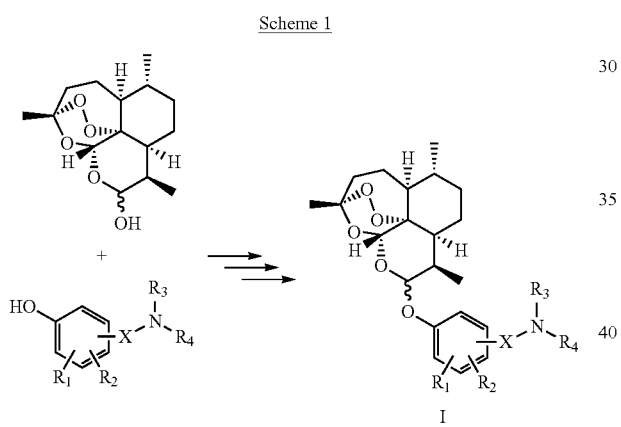

Scheme 2

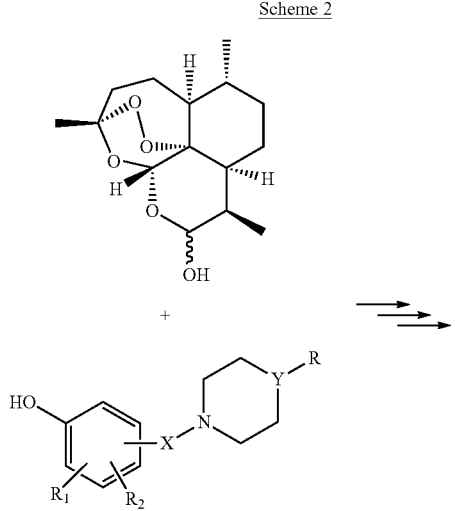

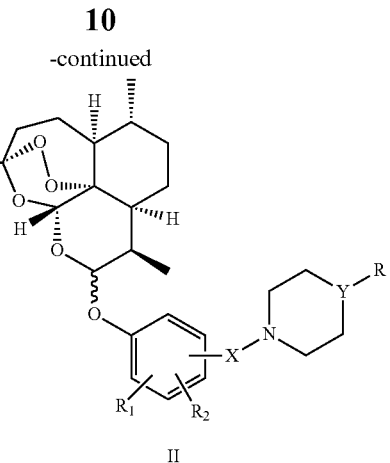

According to the derivatives of Formula I or II of the invention, the substituents are as defined in the Summary of the Invention in Schemes 1 and 2.

The schemes provide a product with a stable yield and a high purity, and the raw materials are easily available.

DETAILED DESCRIPTION OF THE INVENTION

The following Examples are given for the purpose of illustrating this invention and are not intended to limit the scope thereof in any way. The Nuclear magnetic resonance mass spectra of the derivatives were determined with Bruker ARX-300/ARX-600, and the mass spectra were determined with Agilent 1100 LC/MSD; the reagents used were analytical or chemically pure.

Example 1: Preparation of (10S)—O-[4-((pyrrolidin-1-yl)methyl)phenyl]-dihydroartemisinin Step A: Preparation of 4-(pyrrolidin-1-yl)methyl)phenol

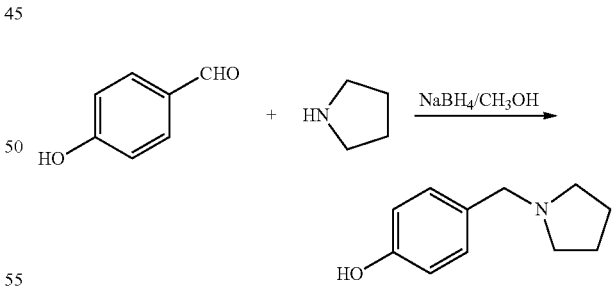

1.22 g (0.01 mol) 4-hydroxybenzaldehyde was dissolved in 30 mL absolute methanol, and 1.25 mL (0.015 mol) pyrrolidine was added thereto under stirring. After stirring for 30 min at room temperature, 0.38 g (0.01 mol) sodium borohydride was added in several portions. After completion of the addition, the reaction was stirred until the starting material point disappeared. The solution was concentrated under reduced pressure, and then was recrystallized in ethanol-water to give a brick red powdered solid with a yield of 78.2%.

Step B: Preparation of dihydroartemisinin-(10S)—O-trifluoroacetic ester

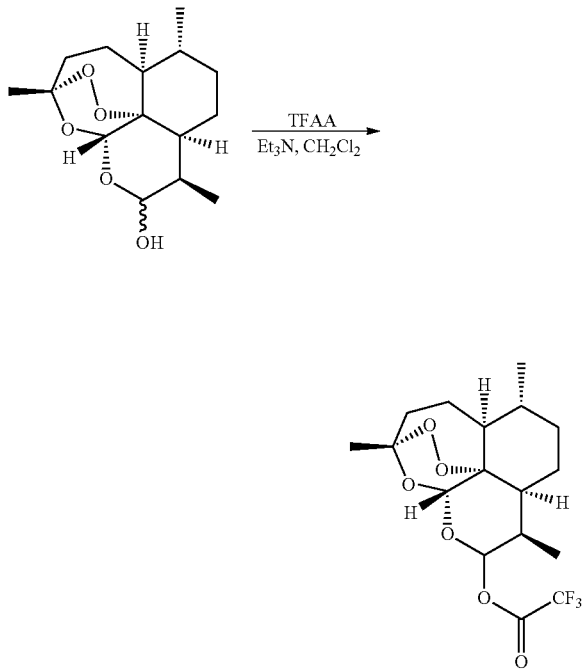

2.84 g (0.01 mol) DHA, 1.52 g (0.015 mol) triethylamine, and 50 mL refined CH₂—Cl₂ were stirred together for 30 minutes in ice-salt bath. Then, 3.15 g (0.15 mol) trifluoroacetic anhydride (TFAA) was added dropwise. The mixture was stirred and reacted until disappearance of dihydroartemisinin raw material as monitored by TLC, which was ready for use without any treatment.

Step C: Preparation of (10S)—O-[4-((pyrrolidin-1-yl)methyl)phenyl]-dihydroartemisinin

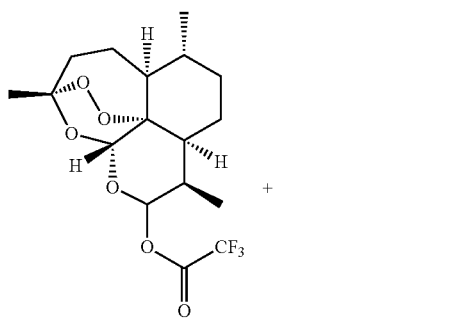

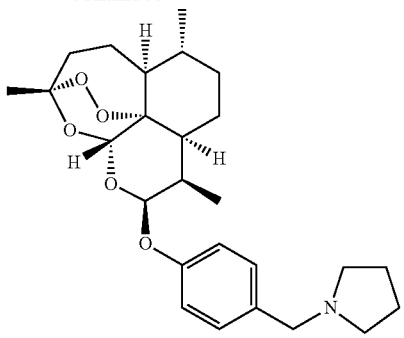

0.89 g (0.005 mol) 4-((pyrrolidin-1-yl)methyl)phenol was added to the above prepared solution of the artemisinin active ester, and stirred at room temperature for 24 hrs. The resulting solution was washed with 5% sodium hydroxide aqueous solution (3×30 mL), 50 mL water and 50 mL of saturated aqueous sodium chloride solution successively. The CH₂Cl₂ layer was dried over anhydrous sodium sulfate overnight. After filtration of the desiccant, the filtrate was concentrated under reduced pressure, and then was separated by silica gel column chromatography (petroleum ether: ethyl acetate=3:1) to give a light yellow solid with a yield of 11.5%, mp: 52-55° C.

MS: (M+H) 444.4;

$^1$H-NMR (300 MHz, DMSO-d$_6$): 0.91 (d, 3H), 0.96 (d, 3H), 1.28 (s, 3H), 1.62 (m, 1H), 1.65 (m, 1H), 1.89 (m, 4H), 1.98 (m, 1H), 2.02 (m, 1H), 2.19 (m, 1H), 2.61 (m, 1H), 3.05 (m, 2H), 4.14 (s, 2H), 5.41 (s, 1H), 5.60 (d, 1H), 7.11 (d, 2H), 7.46 (d, 2H).

Example 2: Preparation of (10S)—O-[4-((imidazol-1-yl)methyl)phenyl]-dihydroartemisinin

Step A: Preparation of 4-((imidazol-1-yl)methyl)phenol

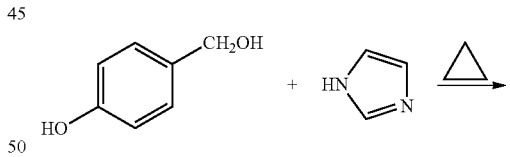

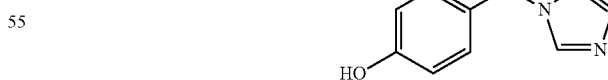

1.24 g (0.01 mol) 4-(hydroxymethyl)phenol and) 1.02 g (0.015 mol) imidazole were added into a round bottom flask, and reacted in a molten state at 90° C. After the mixture was cooled to room temperature naturally, 30 ml ethyl acetate was added thereto, and A lot of solid was precipitated. After suction filtration, filter cake was washed with ethyl acetate and dried under infrared light to give a white powdered solid with a yield of 82.8%.

Step B: Preparation of dihydroartemisinin-(10S)—O-trifluroacetic ester

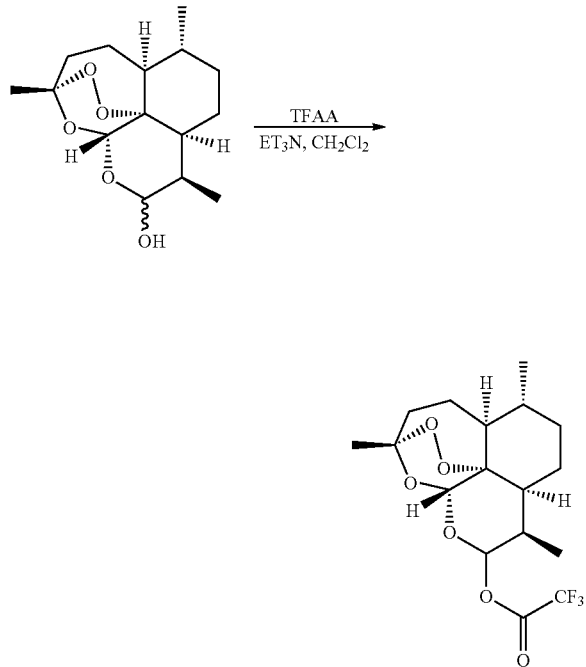

2.84 g (0.01 mol) DHA, 1.52 g (0.015 mol) triethylamine, and 50 mL refined CH$_2$Cl$_2$ were stirred for 30 min in an ice salt bath. After that, 3.15 g (0.015 mol) trifluoroacetic anhydride (TFAA) was added dropwise. The mixture was stirred and reacted until disappearance of the dihydroartemisinin raw material as monitored by TLC, which was ready for use without any treatment.

Step C: Preparation of (10S)—O-[4-((imidazol-1-yl)methyl)phenyl]-dihydroartemisinin

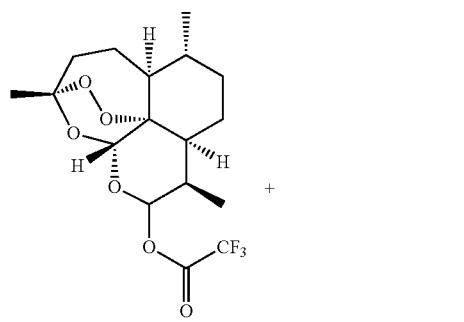

+

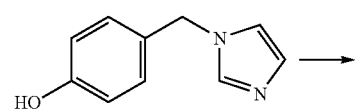

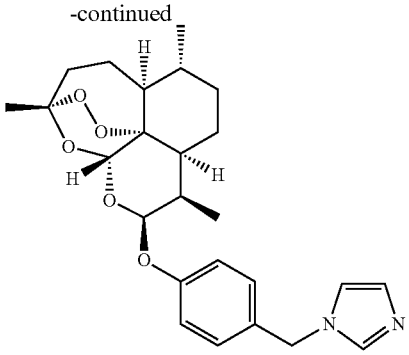

0.87 g (0.005 mol) 4-((imidazol-1-yl)methyl)phenol was added to the above prepared solution of the artemisinin active ester, and stirred for 24 hrs at room temperature. The resulting solution was washed with 5% sodium hydroxide aqueous solution (3×30 mL), 50 mL water and 50 mL of saturated aqueous sodium chloride solution successively. The CH$_2$Cl$_2$ layer was dried over anhydrous sodium sulfate overnight. After filtration of the desiccant, the filtrate was concentrated under reduced pressure, and then was separated by silica gel column chromatography (petroleum ether:ethyl acetate=3:1) to give a white solid product with a yield of 17.5%, mp: 65-67° C.

MS: (M+H) 441.3;

$^1$H-NMR (300 MHz, DMSO-d$_6$): 0.90 (d, J=6.3 Hz, 3H), 0.95 (d, J=7.2 Hz, 3H), 1.27 (s, 3H), 1.82 (m, 1H), 2.00 (m, 1H), 2.18 (m, 1H), 2.58 (m, 1H), 5.12 (s, 2H), 5.39 (s, 1H), 5.54 (d, J=3.3 Hz, 1H), 7.04 (d, J=8, 1 Hz, 2H), 7.23 (d, J=8, 1 Hz, 2H).

In accordance with the preparation method of Example 2, the compounds of Examples 3 and 4 were prepared by selecting appropriate raw materials.

Example 3: Preparation of (10S)—O-[4-((1,2,3-triazol-1-yl)methyl)phenyl]-dihydroartemisinin According to the preparation method of Example 2, the title compound was prepared by using 1,2,3-triazol instead of imidazole in Example 2, mp: 148-151° C.

MS: (M+H) 442.4, (M+Na) 464.3, (2M+H) 884.0;

$^1$H-NMR (300 MHz, DMSO-d$_6$): 8.15 (1H, d, J=0.9 Hz), 7.72 (1H, d, J=0.9 Hz), 7.29 (2H, d, J=8.7 Hz), 7.06 (2H, d, J=8.7 Hz), 5.54 (1H, d, J=3.3 Hz), 5.54 (2H, s), 2.59 (1H, m), 2.18 (1H, m), 2.01 (1H, m), 1.82 (1H, m), 1.27 (3H, s), 0.95 (3H, d, J=7.5 Hz), 0.89 (3H, d, J=6.3 Hz).

Example 4: Preparation of (10S)—O-[4-((1,2,4-triazol-1-yl)methyl)phenyl]-dihydroartemisinin According to the preparation method of Example 2, the title compound was prepared by using 1,2,4-triazol instead of imidazole in Example 2, mp: 164-168° C.

MS: (M+H) 442.4, (M+Na) 464.3, (2M+H) 884.0;

$^1$H-NMR (300 MHz, DMSO-d$_6$): 8.63 (1H, s) 7.96 (1H, s), 7.27 (2H, d, J=8.7 Hz), 7.05 (2H, d, J=8.7 Hz), 5.54 (1H, d, J=3.0 Hz), 5.39 (1H, s), 5.34 (2H, s), 2.58 (1H, m), 2.18 (1H, m), 2.01 (1H, m), 1.82 (1H, m), 1.28 (3H, s), 0.95 (3H, d, j=7.2 Hz), 0.89 (3H, d, J=6.3 Hz).

Example 5: Preparation of (10S)—O-[4-((piperidin-1-yl)methyl)phenyl]-dihydroartemisinin

Step A: Preparation of 4-((piperidin-1-yl)methyl)phenol

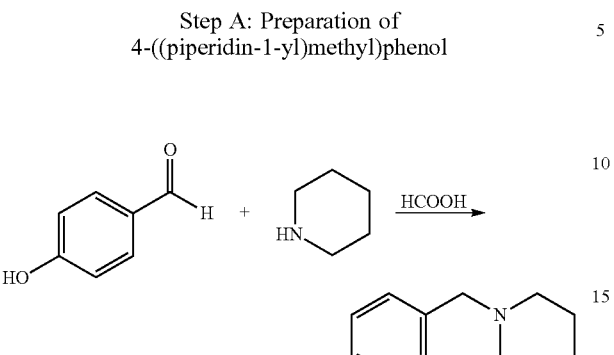

1.22 g (0.01 mol) 4-hydroxybenzaldehyde and 0.85 g (0.01 mol) piperidine were added into a round bottom flask, and reacted in a molten state at 60° C. 0.46 g (0.01 mol) formic acid was slowly added thereto dropwise. After completion of the addition, the mixture was heated to 90° C. and reacted for 2 hrs under reflux. Then the mixture was cooled to room temperature naturally, and 30 ml ethyl acetate was added, a lot of brown solids were insoluble in ethyl acetate. After suction filtration, the filter cake was washed with 30 ml ethyl acetate and dried under the infrared light to give a brown solid with a yield of 21%.

Step B: Preparation of dihydroartemisinin-(10S)—O-trifluoroacetic ester

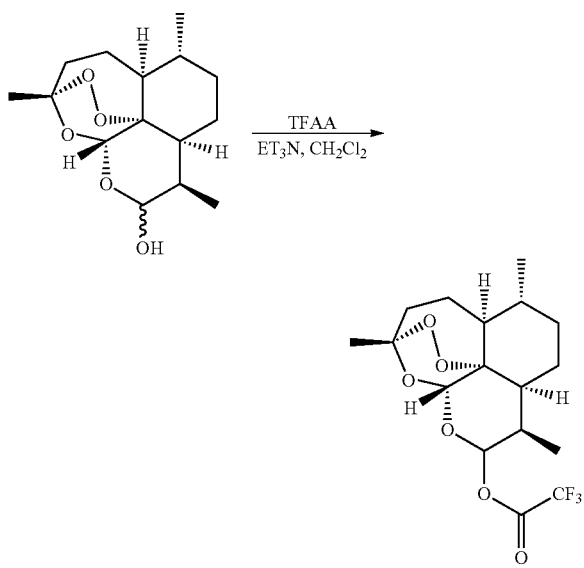

2.84 g (0.01 mol) DHA, 1.52 g (0.015 mol) triethylamine, and 50 mL refined $CH_2Cl_2$ were stirred for 30 min in an ice salt bath. Then, 3.15 g (0.015 mol) trifluoroacetic anhydride (TFAA) was added dropwise. The mixture was stirred and reacted until disappearance of the starting material dihydroartemisinin as monitored by TLC, which was ready for use without any treatment.

Step C: Preparation of (10S)—O-[4-((piperidine-1-yl)methyl)phenyl]-dihydroartemisinin

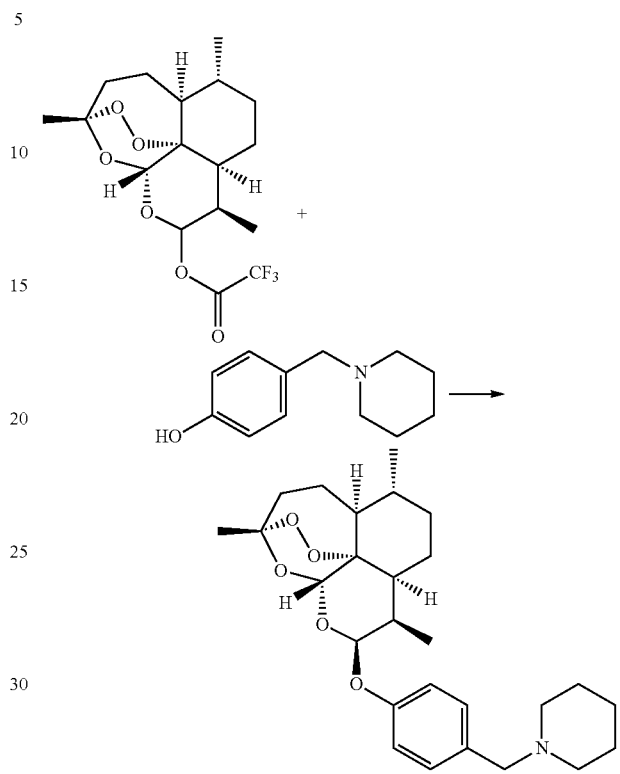

0.96 g (0.005 mol) 4-((piperidin-1-yl)methyl)phenol was added to the above prepared solution of the artemisinin active ester, and stirred for 24 hrs at room temperature. The resulting solution was washed with 5% sodium hydroxide aqueous solution (3×30 mL), 50 mL water and 50 mL of a saturated aqueous sodium chloride solution successively. The $CH_2Cl_2$ layer was dried over anhydrous sodium sulfate overnight. After filtration of the desiccant, the filtrate was concentrated under reduced pressure, and then was separated by silica gel column chromatography (petroleum ether: ethyl acetate=15-10:1) to give brown oil with a yield of 8.4%.

MS: (M+H) 458.5;

$^1$H-NMR (300 MHz, $CDCl_3$): 7.27 (d 2H), 7.07 (d, 2H), 5.48 (d, 1H), 5.48 (s, 1H), 3.73 (m, 2H), 3.70 (m, 4H), 2.82 (m, 1H), 2.63 (m, 4H), 2.38 (m, 1H), 2.02 (m, 1H), 1.94 (m, 1H), 1.46 (s, 3H), 1.02 (d, 3H), 0.97 (d, 3H).

According to the preparation method of Example 5, the compounds of Examples 6-19 were prepared by choosing appropriate raw materials.

Example 6: Preparation of (10S)—O-[4-[(4-(piperidinyl)piperidin-1-yl)methyl]phenyl]-dihydroartemisinin According to the preparation method of Example 5, the title compound was prepared by using 4-(piperidin-1-yl)piperidine instead of piperidine, as a brown powdered solid, m.p.: 125-127° C.

MS: (M+H) 541.5;

$^1$H-NMR (300 MHz, $CDCl_3$): 7.20 (d 2H), 7.06 (d, 2H), 5.49 (d, 1H), 5.49 (s, 1H), 3.69 (m, 2H), 3.35 (m, 6H), 2.83

(m, 1H), 2.80 (m, 2H), 2.38 (m, 1H), 2.05 (m, 1H), 1.92 (m, 1H), 1.44 (s, 3H), 1.02 (d, 3H), 0.97 (d, 3H).

Example 7: Preparation of (10S)—O-[4-((4-methyl-piperazin-1-yl)methyl)phenyl]-dihydroartemisinin According to the preparation method of Example 5, the title compound was prepared by using 4-methylpiperazine instead of piperidine, as a brown powdered solid, m.p.: 45-46° C.
MS: (M+H) 473.5;
$^1$H-NMR (300 MHz, CDCl$_3$): 7.26 (d 2H), 7.10 (d, 2H), 5.50 (d, 1H), 5.47 (s, 1H), 3.83 (m, 2H), 3.34 (m, 2H), 3.12 (m, 4H), 2.81 (m, 1H), 2.75 (m, 2H), 2.39 (m, 1H), 2.04 (m, 1H), 1.93 (s, 1H), 1.44 (d, 3H), 1.02 (d, 3H), 0.97 (d, 3H).

Example 8: Preparation of (10S)—O-[4-((4-ethyl-piperazin-1-yl)methyl)phenyl]-dihydroartemisinin According to the preparation method of Example 5, the title compound was prepared by using 4-ethylpiperazine instead of piperidine, as brown oil.
MS: (M+H) 487.5;
$^1$H-NMR (300 MHz, CDCl$_3$): 7.20 (d 2H), 7.06 (d, 2H), 5.48 (d, 1H), 5.39 (s, 1H), 3.52 (m, 2H), 2.82 (m, 1H), 2.78 (m, 8H), 2.39 (m, 1H), 2.05 (m, 1H), 1.92 (m, 1H), 1.44 (m, 3H), 1.01 m, 3H), 0.96 (d, 3H), 0.92 (d, 3H).

Example 9: Preparation of (10S)—O-[4-((4-isopropylpiperazin-1-yl)methyl)phenyl]-dihydroartemisinin According to the preparation method of Example 5, 4-isopropylpiperazine instead of piperidine was used as the raw materials. Brown powdered solid as the desired final product was obtained. mp: 130-131° C.
MS: (M+H) 501.5;
$^1$H-NMR (300 MHz, CDCl$_3$): 7.24 (d 2H), 7.09 (d, 2H), 5.50 (d, 1H), 5.50 (s, 1H), 3.57 (m, 2H), 3.48 (m, 4H), 2.93 (m, 4H), 2.83 (m, 1H), 2.39 (m, 1H), 2.05 (m, 1H), 1.94 (m, 1H), 1.44 (s, 3H), 1.26 (d, 3H), 1.02 (d, 3H).

Example 10: Preparation of (10S)—O-[4-[(4-((4-phenylpiperazin-1-yl)methyl]phenyl]-dihydroartemisinin According to the preparation method of Example 5, the title compound was prepared by using 4-phenylpiperazine instead of piperidine, as a brown powdered solid, mp: 52-53° C.
MS: (M+H) 535.5;
$^1$H-NMR (300 MHz, CDCl$_3$): 7.27 (d 2H), 7.08 (d, 2H), 6.92 (d, 2H), 6.87 (m, 1H), 5.50 (d, 1H), 5.50 (s, 1H), 3.49 (m, 2H), 3.21 (m, 4H), 2.81 (m, 1H), 2.60 (m, 4H), 2.38 (m, 1H), 2.01 (m, 1H), 1.92 (m, 1H), 1.44 (s, 3H), 1.02 (d, 3H), 0.96 (d, 3H).

Example 11: Preparation of (10)-O-[4-[(4-(2-methoxyphenyl)piperazin-1-yl)methyl]phenyl](10S)-dihydroartemisinin According to the preparation method of Example 5, the title compound was prepared by using 4-(2-methoxyphenyl) piperazine instead of piperidine, as a white solid, mp: 135-137° C.
MS: (M+H) 565.3, (2M+Na$^+$) 1129;
$^1$H-NMR (300 MHz, DMSO-d$_6$): 7.26 (2H, d, J=8.1 Hz), 7.03 (2H, d, J=8.4 Hz), 6.92 (2H, d, J=8.1 Hz), 6.87 (2H, d, J=8.4 Hz), 5.53 (1H, d, J=3.0 Hz), 5.43 (1H, s), 3.76 (4H, s), 3.48 (2H, s), 2.95 (4H, s), 2.58 (1H, m), 2.19 (1H, m), 2.09 (3H, s), 2.02 (1H, m), 1.84 (1H, m), 1.29 (3H, 2), 0.97 (3H, d, J=7.2 Hz), 0.91 (3H, d, J=6.0 Hz).

Example 12: Preparation of (10S)—O-[4-((4-methylpiperazin-1-yl)methyl)phenyl]-dihydroartemisinin According to the preparation method of Example 5, the title compound was prepared by using 4-(3-trifluoromethylphenyl)piperazine instead of piperidine, as a light yellow solid, mp: 65-67° C.
MS: (M+H) 603.2, (M+Na$^+$) 625.2;
$^1$H-NMR (300 MHz, DMSO-d$_6$): 7.40 (1H, t), 7.26 (2H, d, J=8.4 Hz), 7.19 (1H, d, J=8.4 Hz), 7.13 (1H, s), 7.05 (1H, d, J=8.4 Hz), 7.03 (2H, d, J=8.4 Hz), 5.53 (1H, d, J=3.0 Hz), 5.43 (1H, s), 3.47 (2H, s), 3.21 (4H, s), 2.59 (1H, m), 2.50 (4H, s), 2.19 (1H, m), 2.02 (1H, m), 1.84 (1H, m), 1.28 (3H, s, 0.97 (3H, d, J=7.2 Hz), 0.91 (3H, d, J=6.3 Hz).

Example 13: Preparation of 10-O-[4-[(4-(4-flurophenyl)piperazin-1-yl)piperazin-1-yl)methyl]phenyl]-(10S)-dihydroartemisinin According to the preparation method of Example 5, the title compound was prepared by using 4-(4-flurophenyl) piperazine instead of piperidine, as a white solid. mp: 71-73° C.
MS: (M+H) 553.5, (M+Na$^+$) 575.4, (2M+H) 1105.4;
$^1$H-NMR (300 MHz, DMSO-d$_6$): 7.26 (2H, d, J=8.7 Hz), 7.04 (2H, d, J=8.4 Hz), 7.01 (2H, d, J=8.7 Hz), 6.93 (2H, d, J=8.4 Hz), 5.53 (1H, d, j=3.3 Hz), 5.43 (1H, s), 3.46 (2H, s), 3.06 (4H, s), 2.60 (1H, m), 2.50 (4H, s), 2.19 (1H, m), 2.02 (1H, m), 1.85 (1H, m), 1.29 (3H, s), 0.97 (3H, d, J=7.2 Hz), 0.91 (3H, d, J=6.3 Hz).

Example 14: Preparation of 10-O-[4-[(4-(2-pyridyl) piperazin-1-yl)methyl]phenyl]-(10S)-dihydroartemisinin According to the preparation method of Example 5, the title compound was prepared by using 4-(2-pyridyl)piperazine instead of piperidine, as a light yellow solid, mp: 68-70° C.
MS: (M+H) 536.3;
$^1$H-NMR (300 MHz, DMSO-d$_6$): 8.08 (1H, d, J×1.5 Hz), 7.51 (1H, m), 7.26 (2H, d, J=8.4 Hz), 7.03 (2H, d, J=8.4 Hz), 6.78 (1H, d, j=8.4 Hz), 6.62 (1H, m), 5.53 (1H, d, J=3.3 Hz), 5.43 (1H, s), 3.45 (2H, s), 3.41 (4H, s), 2.60 (1H, m), 2.43 (4H, m), 2.19 (1H, m), 2.02 (1H, m), 1.85 (1H, m), 1.29 (3H, s), 1.08 (3H, d, J=7.2 Hz), 0.97 (3H, d, J=7.5 Hz).

Example 15: Preparation of 10-O-[4-[(4-(2-pyrimidinyl)piperazin-1-yl)methyl]phenyl]-(10S)-dihydroartemisinin According to the preparation method of Example 5, the title compound was prepared by using 4-(2-pyrimidinyl) piperazine instead of piperidine, as a light yellow solid, mp: 63-65° C.
MS: (M+H) 536.3;
$^1$H-NMR (300 MHz, DMSO-d$_6$): 8.34 (2H, d, J=4.5 Hz), 7.26 (2H, d, J=8.4 Hz), 7.03 (2H, d, J=8.4 Hz), 6.60 (1H, t), 5.53 (1H, d, J=3.3 Hz), 5.43 (1H, s), 3.71 (4H, s), 3.44 (2H, s), 2.60 (1H, m), 2.40 (4H, s), 2.19 (1H, m), 2.02 (1H, m), 1.85 (1H, m), 1.29 (3H, s), 0.97 (3H, d, J=7.2 Hz), 0.91 (3H, d, J=6.0 Hz).

Example 16: Preparation of 10-O-[4-[(4-benzylpiperazin-1-yl)methyl]phenyl]-(10S)-dihydroartemisinin According to the preparation method of Example 5, the title compound was prepared by using 4-benzylpiperazine instead of piperidine, as brown oil.

MS: (M+H) 549.5;
$^1$H-NMR (300 MHz, CDCl$_3$): 7.32 (m, 6H), 7.11 (m, 3H), 5.50 (d, 1H), 5.45 (s, 1H), 4.01 (5, 2H), 3.49 (m, 2H), 3.49 (m, 4H), 2.82 (m, 1H), 2.80 (m, 4H), 2.38 (m, 1H), 2.01 (m, 1H), 1.92 (m, 1H), 1.44 (s, 3H), 1.01 (d, 3H), 0.96 (d, 3H).

Example 17: Preparation of 10-O-[4-[(4-cinnamylpiperazin-1-yl)methyl]phenyl]-(10S)-dihydroartemisinin According to the preparation method of Example 5, the title compound was prepared by using 4-cinnamylpiperazine instead of piperidine, as a brown powdered solid, mp: 50-51° C.

MS: (M+H) 575.7;
$^1$H-NMR (300 MHz, CDCl$_3$): 7.35 (d, 2H), 7.29 (d, 2H), 7.21 (m, 3H), 7.03 (d, 2H), 6.51 (d, 1H), 6.26 (d, 1H), 5.47 (d, 1H), 5.47 (s, 1H), 3.47 (m, 2H), 3.19 (m, 2H), 2.82 (m, 1H), 2.78 (m, 4H), 2.78 (m, 2H), 2.38 (m, 1H), 2.04 (m, 1H), 1.92 (m, 1H), 1.42 (s, 3H), 0.99 (d, 3H), 0.96 (d, 3H).

Example 18: Preparation of 10-O-[3-[(4-phenylpiperazin-1-yl)methyl]phenyl]-(10S)-dihydroartemisinin According to the preparation method of Example 5, the title compound was prepared by using 4-phenylpiperazine and 3-hydroxybenzaldehyde instead of piperidine and 4-hydroxybenzaldehyde respectively, as a white solid, mp: 118-121° C.

MS: (M+H) 535.3;
$^1$H-NMR (300 MHz, DMSO-d$_6$): 7.22 (1H, m), 7.18 (2H, d, J=7.8 Hz), 7.04 (1H, s), 6.99 (2H, d, J=7.8 Hz), 6.91 (2H, d, J=8.4 Hz), 6.76 (1H, t), 5.54 (1H, d, j=3.0 Hz), 5.43 (1H, s), 3.50 (2H, s), 3.13 (4H, s), 2.60 (1H, m), 2.50 (4H, s), 2.19 (1H, m), 2.02 (1H, m), 1.85 (1H, m), 1.28 (3H, s), 0.97 (3H, d, J=7.2 Hz), 0.91 (3H, d, J=6.3 Hz).

Example 19: Preparation of 10-O-[3-[4-benzylpiperazin-1-yl) methyl]phenyl]-)10S)-dihydroartemisinin According to the preparation method of Example 5, the title compound was prepared by using 4-benzylpiperazine and 3-hydroxybenzaldehyde instead of piperidine and 4-hydroxybenzaldehyde respectively, as a white solid, mp: 61-63° C.

MS: (M+H) 549.3;
$^1$H-NMR (300 MHz, DMSO-d$_6$): 7.31 (1H, m), 7.28 (2H, d, J=7.8 Hz), 7.26 (1H, s), 7.24 (2H, d, J=7.8 Hz), 6.97 (1H, t), 6.92 (2H, d, J=7.8 Hz), 5.52 (1H, d, J=3.3 Hz), 5.41 (1H, s), 3.45 (2H, s), 3.43 (2H, s), 3.34 (4H, s), 2.59 (1H, m), 2.38 (4H, s), 2.20 (1H, m), 2.01 (1H, m), 1.88 (1H, m), 1.27 (3H, s), 0.96 (3H, d, J=7.2 Hz), 0.91 (3H, d, J=6.3 Hz).

Example 20: Preparation of (10S)—O-{4-[3-oxo-3-(pyrrolidin-1-yl)-1-(E)-propen-1-yl]phenyl}-dihydroartemisinin Step A: Preparation of (E)-3-(4-hydroxyphenyl)-1-(pyrrolidin-1-yl)prop-2-en-1-one

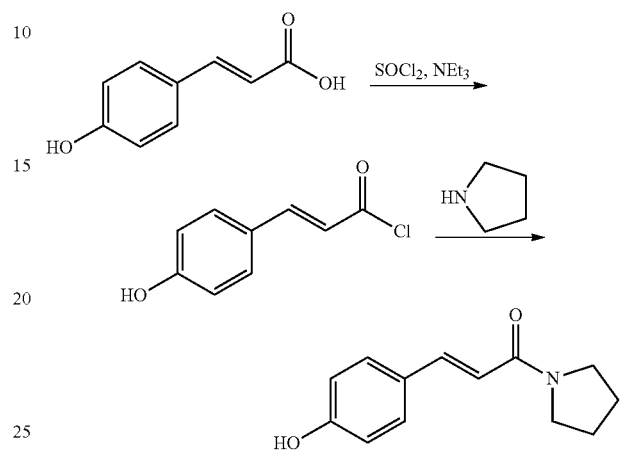

1.64 g (0.01 mol) p-hydroxycinnamic acid and 1.012 g (0.01 mol) triethylamine were dissolved in 30 mL refined CH$_2$Cl$_2$, and then the mixture was stirred for 20 min under reflux, 0.87 mL (0.012) mol) thionyl chloride was slowly added dropwise, and the mixture was continued to stir for 2 hr under reflux. After the mixture was cooled to room temperature naturally, the solvent was evaporated to dry to give a yellow solid. The yellow solid obtained was dissolved in 30 mL refined CH$_2$Cl$_2$, and 0.78 g (0.011 mol) pyrrolidine was added thereto. The reaction was stirred under reflux, and then the solvent was evaporated under reduced pressure to give a white solid with a yield of 56.5%.

Step B: Preparation of dihydroartemisinin-(10S)—O-trifluoroacetic ester

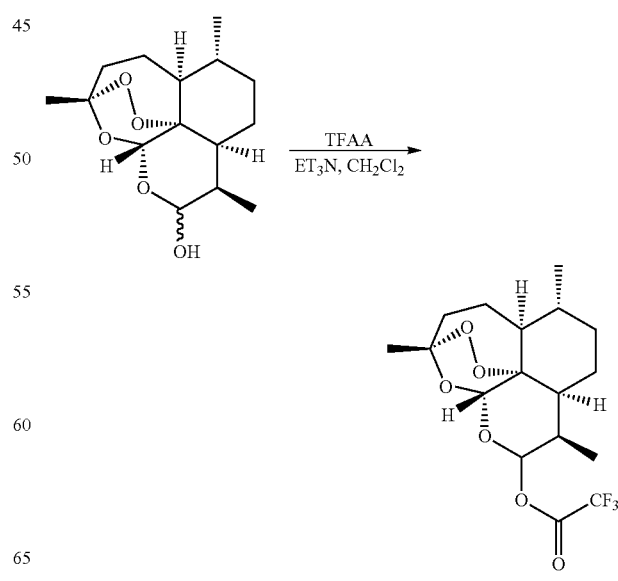

2.84 g (0.01 mol) DHA, 1.52 g (0.015 mol) triethylamine, and 50 mL refined $CH_2Cl_2$ were stirred for 30 min in an ice salt bath. After that, 3.15 g (0.015 mol) trifluoroacetic anhydride (TFAA) was added dropwise, and the reaction was stirred until the disappearance of the starting material dihydroartemisinin as monitored by TLC, which was ready for use without any treatment.

Step C: Preparation of (10S)—O-{4-[3-oxo-3-(pyrrolidin-1-yl)-1-(E)-propen-1-yl]phenyl}-dihydroartemisinin

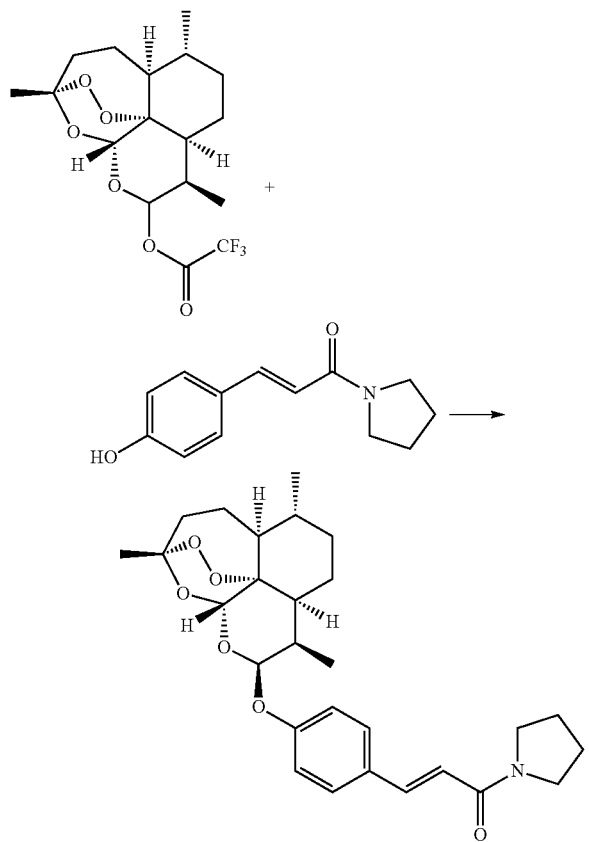

1.09 g (0.005 mol) (E)-3-(4-hydroxyphenyl)-1-(pyrrolidin-1-yl)prop-2-en-1-one was added to the above prepared solution of the artemisinin active ester, and the reaction was stirred for 24 hr at room temperature. The resulting solution was washed with 5% sodium hydroxide aqueous solution (3×30 mL), 50 mL water and 50 mL of a saturated aqueous sodium chloride solution successively. The $CH_2Cl_2$ layer was dried over anhydrous sodium sulfate overnight. After filtration of the desiccant, the filtrate was concentrated under reduced pressure, and then was separated by silica gel column chromatography (petroleum ether:ethyl acetate=3~1:1) to give a white solid with a yield of 10.3%, mp: 165-167° C.

MS: (M+H) 484, (M+Na) 506;

$^1$H-NMR (300 MHz, DMSO-$d_6$): 7.65 (2H, d, J=8.4 Hz), 7.43 (1H, d, J=15.3 Hz), 7.09 (2H, d, J=8.4 Hz), 6.85 (1H, d, J=15.3 Hz), 5.63 (1H, d, J=3.0 Hz), 5.40 (1H, s), 3.62 (2H, m), 3.39 (2H, m), 2.61 (1H, m), 2.19 (1H, m), 2.02 (1H, m), 1.89 (1H, m), 1.82 (4H, m), 1.29 (3H, s), 0.97 (3H, d, J=7.2 Hz), 0.91 (3H, d, J=6.0 Hz).

According to the preparation method of Example 20, the compounds of Examples 21-30 were prepared by choosing appropriate raw materials.

Example 21: Preparation of (10S)—O-{4-[3-oxo-3-(morpholin-4-yl)-1-(E)-propen-1-yl]phenyl}-dihydroartemisinin According to the preparation method of Example 20, the title compound was prepared by using the raw material morpholine instead of pyrrolidine, as a white solid, mp: 85-86° C.

MS: (M+H) 500.6;

$^1$H-NMR (300 MHz, DMSO-$d_6$): 7.68 (2H, d, J=8.4 Hz), 7.48 (1H, d, J=15.3 Hz), 7.13 (1H, d, J=15.3 Hz), 7.09 (2H, d, J=8.4 Hz), 5.64 (1H, d, J=3.0 Hz), 5.41 (1H, s), 3.70 (2H, m), 3.60 (6H, m), 2.62 (1H, m), 2.19 (1H, m), 2.02 (1H, m), 1.84 (1H, m), 1.29 (3H, s), 0.97 (3H, d, J=7.2 Hz), 0.91 (3H, d, J=6.0 Hz).

Example 22: Preparation of (10S)—O-{4-[3-oxo-3-(piperidin-1-yl)-1-(E)-propen-1-yl]phenyl}-dihydroartemisinin According to the preparation method of Example 20, the title compound was prepared by using the raw material piperidine instead of pyrrolidine, as a white solid, mp: 165-167° C.

MS: (M+H) 498.4; (M+Na) 520.3;

$^1$H-NMR (300 MHz, DMSO-$d_6$): 7.62 (1H, d, J=15.3 Hz), 7.47 (2H, d, J=8.4 Hz), 7.12 (2H, d, J=8.4 Hz), 6.80 (1H, d, J=15.3 Hz), 5.54 (1H, d, J=2.1 Hz), 5.48 (1H, s), 3.64 (4H, s), 2.83 (1H, m), 2.39 (1H, m), 2.07 (1H, m), 1.95 (1H, m), 1.65 (4H, m), 1.45 (3H, s), 1.03 (3H, d, J=7.2 Hz), 0.97 (3H, d, J=6.0 Hz).

Example 23: Preparation of (10S)—O-{4-[3-oxo-3-(4-(piperidin-1-yl)piperidine-1-(E)-propen-1-yl]phenyl}-dihydroartemisinin According to the preparation method of Example 20, the title compound was prepared by using the raw material 4-(piperidin-1-yl)piperidine instead of pyrrolidine, as a white solid, mp: 125-126° C.

MS: (M+H) 581.5; (M+Na) 603.5;

$^1$H-NMR (300 MHz, DMSO-$d_6$): 7.69 (2H, d, J=8.7 Hz), 7.45 (1H, d, J=15.3 Hz), 7.15 (1H, d, J=15.3 Hz), 7.09 (2H, d, J=8.7 Hz), 5.63 (1H, d, J=3.0 Hz), 5.40 (1H, s), 4.54 (1H, m), 4.36 (1H, m), 3.01 (4H, m), 2.74 (4H, m), 2.61 (1H, m), 2.19 (1H, m), 2.03 (1H, m), 1.85 (1H, m), 1.29 (3H, s), 0.97 (3H, d, J=7.2 Hz), 0.91 (3H, d, J=6.0 Hz).

Example 24: Preparation of (10S)—O-{4-[3-oxo-3-(4-methylpiperazin-1-yl-1-(E)-propen-1-yl]phenyl}-dihydroartemisinin According to the preparation method of Example 20, the title compound was prepared by using the raw material 4-methylpiperazine instead of pyrrolidine, as a brown solid. mp: 92-93° C.

MS: (M+H) 515.5:

$^1$H-NMR (300 MHz, CDCl$_3$): 7.64 (1H, d, J=15.3 Hz), 7.46 (2H, d, J=8.7 Hz), 7.11 (2H, d, J=8.7 Hz), 6.74 (1H, d, J=15.3 Hz), 5.53 (1H, d, J=3.0 Hz), 5.45 (1H, s), 3.76 (4H, m), 2.82 (1H, m), 2.53 (4H, m), 2.38 (3H, s), 2.32 (1H, m), 2.03 (1H, m), 1.91 (1H, m), 1.72 (1H, d), 1.68 (1H, d), 1.43 (3H, s), 1.02 (3H, d, J=8.4 Hz), 0.96 (3H, d, J=5.7 Hz).

Example 25: Preparation of (10S)—O-{4-[3-oxo-3-(4-ethyl piperazin-1-yl)-1-(E)-propen-1-yl]phenyl}-dihydroartemisinin According to the preparation method of Example 20, the title compound was prepared by using the raw material 4-ethylpiperazine instead of pyrrolidine, as a brown solid, mp: 58-59° C.

MS: (M+H) 527.4, (M+Na⁺) 549.3, (M+K⁺) 565.3:
¹H-NMR (300 MHz. CDCl₃): 7.61 (d, 1H), 7.43 (d, 2H), 7.08 (d, 2H), 6.73 (d, 1H), 5.51 (d, 1H), 5.43 (s, 1H), 3.74 (m, 2H), 3.69 (m, 2H), 2.79 (m, 1H), 2.48 (m, 4H), 2.46 (m, 4H), 2.36 (m, 1H), 2.07 (m, 1H), 1.95 (m, 1H), 1.71 (d, 1H), 1.68 (d, 1H), 1.41 (s, 3H), 1.11 (m, 3H), 0.99 (d, 3H), 0.93 (d, 3H).

Example 26: Preparation of (10S)—O-{4-[3-oxo-3-(4-phenylpiperazin-1-yl)-1-(E)-propen-1-yl]phenyl}-dihydroartemisinin According to the preparation method of Example 20, the title compound was prepared by using the raw material 4-phenylpiperazine instead of pyrrolidine, as a brown solid, mp: 88-89° C.

MS: (M+H) 589.4, (M+Na⁺) 611.3;
¹H-NMR (300 MHz, DMSO-d₆): 7.78 (d, 1H), 7.67 (d, 2H), 7.45 (d, 1H), 7.32 (m, 2H), 7.25 (m, 3H), 7.08 (d, 2H), 5.64 (d, 1H), 5.40 (s, 1H), 3.70 (m, 2H), 3.57 (m, 2H), 3.51 (s, 2H), 2.62 (m, 1H), 2.39 (m, 4H), 2.20 (m, 1H), 2.00 (m, 1H), 1.93 (m, 1H), 1.64 (d, 1H), 1.55 (d, 1H), 1.38 (s, 3H), 0.96 (d, 3H), 0.90 (d, 3H).

Example 27: Preparation of (10S)—O-{4-[3-oxo-3-(4-(2-methoxyphenyl)piperazin-1-yl)-1-(E)-propen-1-yl]phenyl}-dihydroartemisinin According to the preparation method of Example 20, the title compound was prepared by using the raw material 4-(2-methoxyphenyl) piperazine instead of pyrrolidine, as a white solid, mp: 144-146° C.

MS: (M+H) 605.3, (M+Na⁺) 627.3;
¹H-NMR (300 MHz, DMSO-d₆): 7.69 (2H, d, J=8.4 Hz), 7.47 (1H, d, J=15.3 Hz), 7.18 (1H, d, J=15.3 Hz), 7.10 (2H, d, J=8.4 Hz), 6.96 (2H, m), 6.90 (2H, m), 5.64 (1H, d, J=2.4 Hz), 5.41 (1H, s), 3.80 (3H, s), 3.71 (4H, m), 2.97 (4H, s), 2.61 (1H, m), 2.19 (1H, m), 2.01 (1H, m), 1.84 (1H, m), 1.29 (3H, s), 0.96 (3H, d, J=7.2 Hz), 0.90 (3H, d, J=6.0 Hz).

Example 28: Preparation of (10S)—O-{4-[3-oxo-3-(4-(3-trifluoromethylphenyl)piperazin-1-yl)-1-(E)-propen-1-yl]phenyl}-dihydroartemisinin According to the preparation method of Example 20, the title compound was prepared by using the mw material 4-(3-trifluoromethylphenyl)piperazine instead of pyrrolidine, as a white solid, mp: 101-102° C.

MS: (M+H) 643.4, (M+Na⁺) 665.4;
¹H-NMR (300 MHz, DMSO-d₆): 7.70 (2H, d, J=8.7 Hz), 7.50 (1H, d, J=15.3 Hz), 7.43 (1H, d, J=8.4 Hz), 7.26 (1H, d, J=8.4 Hz), 7.22 (1H, s), 7.20 (1H, d, J=15.3 Hz), 7.10 (2H, d, J=8.7 Hz), 7.10 (1H, m), 5.64 (1H, d, J=3.0 Hz), 5.41 (1H, s), 3.85 (4H, m), 3.28 (4H, m), 2.62 (1H, m), 2.19 (1H, m), 2.02 (1H, m), 1.85 (1H, m), 1.29 (3H, s), 0.97 (3H, d, J=7.5 Hz), 0.90 (3H, d, J=6.3 Hz).

Example 29: Preparation of (10S)—O-{4-[3-oxo-3-(4-benzylpiperazin-1-yl)-1-(E)-propen-1-yl]phenyl}-dihydroartemisinin According to the preparation method of Example 20, the title compound was prepared by using the raw material 4-benzylpiperazine instead of pyrrolidine, as a white solid, mp: 98-99° C.

MS: (M+H) 589.5;
¹H-NMR (300 MHz, DMSO-d₆): 7.79 (1H, m), 7.67 (2H, d, J=8.1 Hz), 7.45 (1H, d, J=15.6 Hz), 7.32 (2H, m), 7.26 (2H, m), 7.14 (1H, d, J=15.6 Hz), 7.08 (2H, d, J=8.1 Hz), 5.64 (1H, d, J=3.0 Hz), 5.40 (1H, s), 3.69 (2H, s), 3.54 (4H, m), 2.61 (1H, m), 2.38 (4H, s), 2.15 (1H, m), 2.02 (1H, m), 1.84 (1H, m), 1.29 (3H, s), 0.96 (3H, d, J=6.6 Hz), 0.91 (3H, d, J=6.0 Hz).

Example 30: Preparation of (10S)—O-{4-[3-oxo-3-(4-(2-pyridyl) piperazin-1-yl)-1-(E)-propen-1-yl]phenyl}-dihydroartemisinin According to the preparation method of Example 20, the title compound was prepared by using the raw material 4-(2-pyridyl) piperazine instead of pyrrolidine, as a white solid, mp: 67-69° C.

MS: (M+H) 576.3;
¹H-NMR (300 MHz, DMSO-d₆): 8.23 (1H, d, J=3.3 Hz), 7.72 (1H, d, J=15.3 Hz), 7.57 (1H, d, J=15.3 Hz), 7.54 (3H, m), 7.14 (2H, d, J=8.4 Hz), 6.69 (2H, d, J=8.4 Hz), 5.56 (1H, d, J=3.0 Hz), 5.48 (1H, s), 3.85 (4H, m), 3.65 (4H, m), 2.84 (1H, m), 2.40 (1H, m), 2.07 (1H, m), 1.95 (1H, m), 1.46 (3H, s), 1.04 (3H, d, J=7.2 Hz), 0.98 (3H, d, J=6.0 Hz).

Example 31: Preparation of 4-[(10S)-dihydroartemisinin-10-O-yl]phenyl-acrylic acid-4-[3-oxo-3-(piperidin-1-yl)-1-(E)-propen-1-yl]phenyl ester Step A: Preparation of ρ-hydroxy cinnamic acid-4-3-oxo-3-(piperidin-1-yl)propen-1-yl)phenyl ester

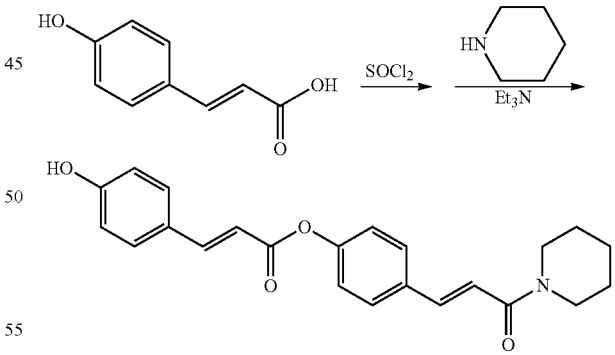

1.64 g (0.01 mol) ρ-hydroxycinnamic acid and 1.012 g (0.01 mol) triethylamine were dissolved in 30 mL refined CH₂Cl₂, and then the mixture was stirred for 20 min under reflux, 0.87 mL (0.012 mol) thionyl chloride was slowly added dropwise, and the mixture was continued to stir for 2 hr under reflux. After the mixture was cooled to room temperature naturally, the solvent was evaporated to dry to give a yellow solid. The yellow solid obtained was dissolved in 30 mL refined CH₂Cl₂, and 0.94 g (0.011 mol) piperidine was added thereto. The reaction was stirred under reflux, and then the solvent was evaporated under reduced pressure to give white solid with a yield of 39.2%.

Step B: Preparation of dihydroartemisinin-(10S)—O-trifluoroacetic ester

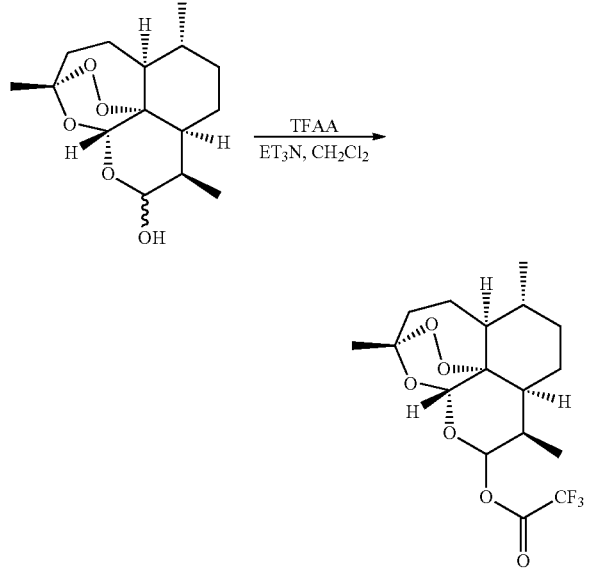

2.84 g (0.01 mol) DHA, 1.52 g (0.015 mol) triethylamine, and 50 mL refined CH$_2$Cl$_2$ were stirred for 30 min in an ice salt bath. After that, 3.15 g (0.015 mol) trifluoroacetic anhydride (TFAA) was added dropwise, and the reaction was stirred until the disappearance of the starting material dihydroartemisinin as monitored by TLC, which was ready for use without any treatment.

Step C: Preparation of 4-[(10S)-dihydroartemisinin-10-O-yl]phenyl-acrylic acid-4-[3-oxo-3-(piperidin-1-yl)-1-(E)-propen-1-yl]phenyl ester

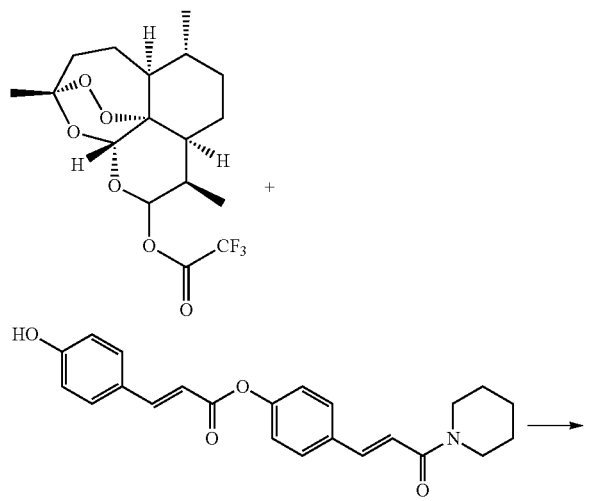

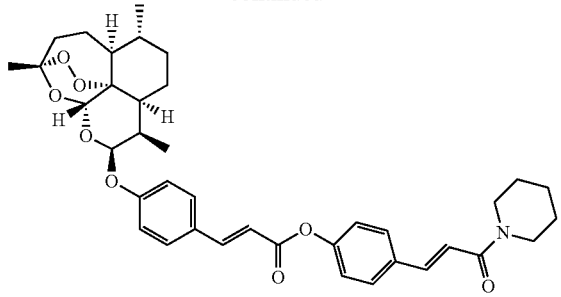

1.78 g (0.005 mol) p-hydroxy cinnamic acid-4-3-oxo-3-(piperidin-1-yl)propen-1-yl)phenyl ester was added to the above prepared solution of the artemisinin active ester, and stirred for 24 hr at room temperature. The resulting solution was washed with 5% sodium hydroxide aqueous solution (3×30 mL), 50 mL water and 50 mL of a saturated aqueous sodium chloride solution successively. The CH$_2$Cl$_2$ layer was dried over anhydrous sodium sulfate overnight. After filtration of the desiccant, the filtrate was concentrated under reduced pressure, and then was separated by silica gel column chromatography (petroleum ether:ethyl acetate=3~1:1) to give a white solid with a yield of 10.3%, mp: 160-163° C.

MS: (M+H) 644.3, (M+Na) 666.3;

$^1$H-NMR (300 MHz, CDCl$_3$): 7.85 (1H, d, J=15.9 Hz), 7.79 (4H, d, J=8.7 Hz), 7.49 (1H, d, J=15.3 Hz), 7.28 (1H, d, J=15.3 Hz), 7.24 (2H, d, J=8.7 Hz), 7.15 (2H, d, J=8.7 Hz), 6.77 (1H, d, J=15.9 Hz), 5.69 (1H, d, J=3.0 Hz), 5.42 (1H, s), 3.60 (4H, m), 2.62 (1H, m), 2.15 (1H, m), 2.02 (1H, m), 1.85 (1H, m), 1.52 (4H, m), 1.30 (3H, s), 0.98 (3H, d, J=7.2 Hz), 0.91 (3H, d, J=6.3 Hz).

Example 32: Preparation of 4-[(10S)-dihydroartemisinin-10-O-yl]phenyl-acrylic acid-4-[3-oxo-3-(4-(2-pyrimidinyl)piperazin-1-yl)-1-(E)-propen-1-yl] phenyl ester According to the preparation method of Example 31, the title compound was prepared by using the raw material 4-(2-pyrimidinyl)piperazine instead of pyrrolidine, as a white solid, mp: 117-119° C.

MS: (M+H) 723.6, (M+Na) 745.7;

$^1$H-NMR (300 MHz, CDCl$_3$): 8.40 (2H, d, J=4.5 Hz), 7.84 (1H, d, J=15.9 Hz), 7.81 (2H, d, J=8.4 Hz), 7.81 (2H, d, J=8.4 Hz), 7.56 (1H, d, J=15.3 Hz), 7.33 (1H, d, J=15.3 Hz), 7.27 (2H, d, J=8.4 Hz), 7.15 (2H, d, J=8.4 Hz), 6.77 (1H, d, J=15.9 Hz), 6.67 (1H, m), 5.69 (1H, d, J=2.4 Hz), 5.42 (1H, s), 3.80 (8H, m), 2.63 (1H, m), 2.16 (1H, m), 2.03 (1H, m), 1.85 (1H, m), 1.30 (3H, s), 0.98 (3H, d, J=6.9 Hz), 0.91 (3H, d, J=6.0 Hz).

Example 33: Preparation of (10S)—O-{4-[2-(pyrrolidin-1-yl)-2-oxoethyl]phenyl}-dihydroartemisinin

Step A: Preparation of 2-(4-hydroxyphenyl)-1-(pyrrolidin-1-yl)ethanone

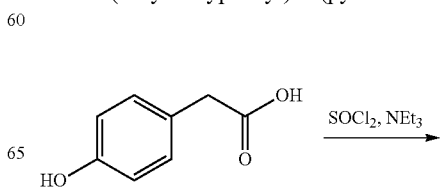

-continued

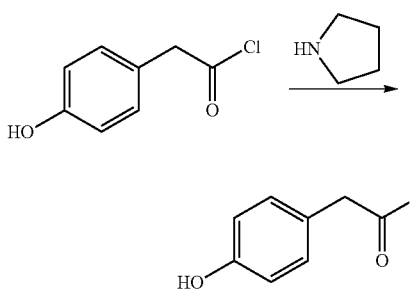

1.52 g (0.01 mol) 2-(4-hydroxyphenyl)acetic acid and 1.012 g (0.01 mol) triethylamine were dissolved in 30 mL refined $CH_2Cl_2$, and then the mixture was stirred for 20 min under reflux, 0.87 mL (0.012 mol) thionyl chloride was slowly added dropwise, and the mixture was continued to stir for 2 hr under reflux. After the mixture was cooled to room temperature naturally, 0.78 g (0.011 mol) pyrrolidine was added thereto, and then the reaction was stirred for 2 hr under reflux. After completion of the reaction, the mixture was separated directly by silica gel column chromatography (methylene dichloride:acetone (v/v)=5~1:1) to give light yellow oil with a yield of 46.7%.

Step B: Preparation of dihydroartemisinin-(10S)—O-trifluoroacetic ester

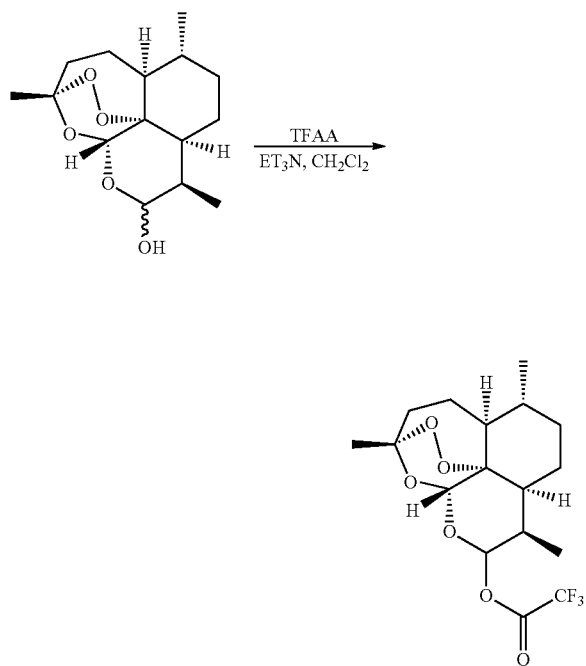

2.84 g (0.01 mol) DHA, 1.52 g (0.015 mol) triethylamine, and 50 mL refined $CH_2Cl_2$ were stirred for 30 min in an ice salt bath. After that, 3.15 g (0.015 mol) trifluoroacetic anhydride (TFAA) was added thereto dropwise, and the reaction was stirred until the disappearance of the starting material dihydroartemisinin as monitored by TLC, which was ready for use without any treatment.

Step C: Preparation of (10S)—O-{4-[2-pyrrolidin-1-yl)-2-oxoethyl]phenyl}-dihydroartemisinin

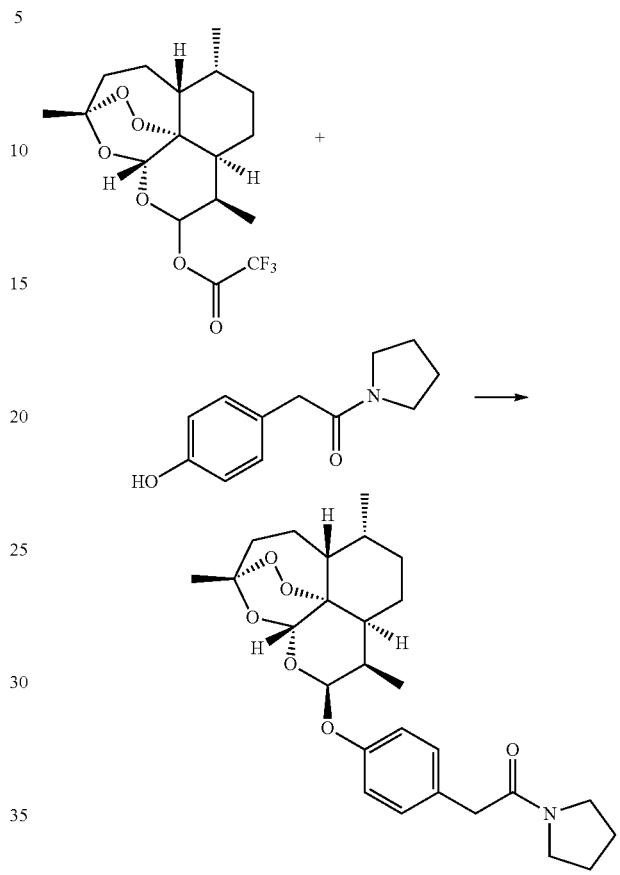

1.03 g (0.005 mol) 2-(4-hydroxyphenyl)-1-(pyrrolidin-1-yl)ethanone was added to the above prepared solution of the artemisinin active ester, and the mixture was stirred for 24 hr at room temperature. The resulting solution was washed with 5% sodium hydroxide aqueous solution (3×30 mL), 50 mL water and 50 mL of a saturated aqueous sodium chloride solution successively. The $CH_2Cl_2$ layer was dried over anhydrous sodium sulfate overnight. After filtration of the desiccant, the filtrate was concentrated under reduced pressure, and then was separated by silica gel column chromatography (methylene dichloride:acetone (v/v)=10-5:1) to give a white solid with a yield of 22.3%, mp: 73-74° C.

MS: (M+H) 472.3, (M+Na) 494.3;

$^1$H-NMR (300 MHz, DMSO-$d_6$): 7.16 (2H, d, J=8.1 Hz), 6.99 (2H, d, J=8.1 Hz), 5.50 (1H, d, J=3.0 Hz), 5.42 (1H, s), 3.54 (2H, s), 3.44 (2H, t), 3.27 (2H, t), 2.57 (1H, m), 2.18 (1H, m), 2.01 (1H, m), 1.85 (1H, m), 1.28 (3H, s), 0.96 (3H, d, J=7.2 Hz), 0.90 (3H, d, J=5.7 Hz).

According to the preparation method of Example 33, the compounds of Examples 34-46 were prepared by choosing appropriate raw materials.

Example 34: Preparation of (10S)—O-{4-[2-(morpholin-4-yl)-2-oxoethyl]phenyl}-dihydroartemisinin According to the preparation method of Example 33, the title compound was prepared by using the raw material morpholine instead of pyrrolidine, as a white solid with a yield of 13.6%, mp: 107-109° C.

MS: (M+H) 483.3, (M+Na) 510.3;
$^1$H-NMR (300 MHz, DMSO-d$_6$): 7.16 (2H, d, J=8.1 Hz), 6.99 (2H, d, J=8.1 Hz), 5.50 (1H, d, J=3.0 Hz), 5.42 (1H, s) 3.54 (2H, s), 3.44 (2H, t), 3.27 (2H, t), 2.57 (1H, m), 2.18 (1H, m), 2.01 (1H, m), 1.85 (1H, m), 1.28 (3H, s), 0.96 (3H, d, J=7.2 Hz), 0.90 (3H, d, J=5.7 Hz).

Example 35: Preparation of (10S)—O-{4-[2-(piperidin-1-yl)-2-oxoethyl]phenyl}-dihydroartemisinin According to the preparation method of Example 33, the title compound was prepared by using the raw material piperidine instead of pyrrolidine, as a white solid with a yield of 11.7%. mp: 130-133° C.
MS: (M+H) 487.3;
$^1$H-NMR (300 MHz, DMSO-d$_6$): 7.15 (2H, d, J=8.4 Hz), 6.99 (2H, d, J=8.4 Hz), 5.50 (1H, d, J=2.7 Hz), 5.42 (1H, s), 3.62 (2H, s), 2.58 (1H, m), 2.19 (1H, m), 2.02 (1H, m), 1.84 (1H, m), 1.53 (2H, m), 1.37 (4H, m), 1.28 (3H, s), 0.96 (3H, d, J=7.2 Hz), 0.90 (3H, d, J=6.0 Hz).

Example 36: Preparation of (10S)—O-{4-[2-(4-methylpiperidin-1-yl)-2-oxoethyl]phenyl}-dihydroartemisinin According to the preparation method of Example 33, the title compound was prepared by using the raw material 4-methylpiperidine instead of pyrrolidine, as a white solid with a yield of 12.4%, mp: 87-89° C.
MS: (M+H) 500.3, (M+Na) 522.2;
$^1$H-NMR (300 MHz, DMSO-d$_6$): 7.15 (2H, d, J=8.7 Hz), 6.99 (2H, d, J=8.7 Hz), 5.50 (1H, d, J=3.0 Hz), 5.42 (1H, s), 4.35 (1H, dd), 4.35 (1H, dd), 3.90 (1H, dd), 3.62 (2H, s), 2.96 (1H, m), 2.58 (1H, m), 2.19 (1H, m), 2.02 (1H, m), 1.84 (1H, m), 1.55 (4H, m), 1.28 (3H, s), 0.96 (3H, d, J=7.5 Hz), 0.91 (3H, d, J=6.3 Hz), 0.86 (3H, d, J=6.3 Hz).

Example 37: Preparation of (10S)—O-{4-[2-(2-methylpiperidin-1-yl)-2-oxoethyl]phenyl}-dihydroartemisinin According to the preparation method of Example 33, the title compound was prepared by using the raw material 2-methylpiperidine instead of pyrrolidine, as a white solid with a yield of 11.1%, mp: 77-81° C.
MS: (M+H) 500.6, (M+Na) 522.6;
$^1$H-NMR (300 MHz, DMSO-d$_6$): 7.14 (2H, d, J=8.4 Hz), 6.99 (2H, d, J=8.4 Hz), 5.50 (1H, d, J=3.0 Hz), 5.43 (1H, s), 4.27 (1H, m), 3.67 (1H, m), 3.60 (2H, s), 2.96 (1H, m), 2.57 (1H, m), 2.19 (1H, m), 2.02 (1H, m), 1.84 (1H, m), 1.55 (4H, m), 1.28 (3H, s), 1.06 (3H, d, J=6.3 Hz), 0.96 (3H, d, J=7.5 Hz), 0.90 (3H, d, J=6.3 Hz).

Example 38: Preparation of (10S)—O-{4-[2-(3,5-dimethylpiperidin-1-yl)-2-oxoethyl]phenyl}-dihydroartemisinin According to the preparation method of Example 33, the title compound was prepared by using the raw material 3,5-dimethylpiperidine instead of pyrrolidine, as a white solid with a yield of 9.4%. mp: 73-76° C.
MS: (M+H) 514.6, (M+Na) 536.6;
$^1$H-NMR (300 MHz, DMSO-d$_6$): 7.16 (2H, d, J=8.7 Hz), 6.99 (2H, d, J=8.7 Hz), 5.50 (1H, d, J=3.0 Hz), 5.42 (1H, s), 4.36 (1H, dd), 3.87 (1H, dd), 3.64 (2H, s), 2.58 (1H, m), 2.19 (1H, m), 2.01 (1H, m), 1.84 (1H, m), 1.84 (1H, m), 1.28 (3H, s), 1.25 (3H, d, J=6.3 Hz), 0.96 (3H, d, J=7.5 Hz), 0.91 (3H, d, J=6.3 Hz), 0.82 (6H, d, J=6.6 Hz).

Example 39: Preparation of (10S)—O-{4-[2-[4-(piperidin-1-yl)piperidin-1-yl]-2-oxoethyl]phenyl}-dihydroartemisinin According to the preparation method of Example 33, the title compound was prepared by using the raw material 4-(piperidin-1-yl)piperidine instead of pyrrolidine, as a white solid with a yield of 16.3%, mp: 99-102° C.
MS: (M+H) 569.3;
$^1$H-NMR (300 MHz, DMSO-d$_6$): 7.15 (2H, d, J=8.7 Hz), 6.99 (2H, d, J=8.7 Hz), 5.50 (1H, d, J=3.0 Hz), 5.42 (1H, s), 4.39 (1H, m), 3.94 (1H, m), 3.63 (2H, s), 2.91 (1H, t), 2.59 (1H, m), 2.36 (6H, m), 2.19 (1H, m), 2.02 (1H, m), 1.84 (1H, m), 1.65 (3H, m), 1.40 (5H, m), 1.28 (3H, s), 0.96 (3H, d, J=7.5 Hz), 0.90 (3H, d, J=6.3 Hz).

Example 40: Preparation of (10S)—O-{4-[2-(4-phenylpiperazin-1-yl)-2-oxoethyl]phenyl}-dihydroartemisinin According to the preparation method of Example 33, the title compound was prepared by using the raw material 4-phenylpiperazine instead of pyrrolidine, as a white solid with a yield of 24.5%. mp: 122-124° C.
MS: (M+H) 563.4, (M+Na) 585.4;
$^1$H-NMR (300 MHz, DMSO-d$_5$): 7.23 (2H, d, J=9.0 Hz), 7.19 (2H, m), 7.01 (2H, d, J=9.0 Hz), 6.93 (2H, d, J=8.1 Hz), 6.80 (1H, m), 5.50 (1H, d, J=3.0 Hz), 5.42 (1H, s), 3.70 (2H, s), 3.62 (4H, m), 3.07 (4H, m), 2.57 (1H, m), 2.19 (1H, m), 2.02 (1H, m), 1.84 (1H, m), 1.28 (3H, s), 0.96 (3H, d, J=7.2 Hz), 0.90 (3H, d, J=6.0 Hz).

Example 41: Preparation of (10S)—O-{4-[2-[4-(2-methoxyphenyl)piperazin-1-yl]-2-oxoethyl]phenyl}-dihydroartemisinin According to the preparation method of Example 33, the title compound was prepared by using the raw material 4-(2-methoxyphenyl) piperazine instead of pyrrolidine, as a white solid with a yield of 10.3%, mp: 99-102° C.
MS: (M+H) 593.3, (M+Na) 615.3;
$^1$H-NMR (300 MHz, DMSO-d$_6$): 7.18 (2H, d, J=8.7 Hz), 7.01 (2H, d, J=8.7 Hz), 6.95 (2H, m), 6.86 (2H, m), 5.50 (1H, d, J=3.3 Hz), 5.43 (1H, s), 3.78 (3H, s), 3.69 (2H, s), 3.61 (4H, m), 2.88 (4H, m), 2.58 (1H, m), 2.19 (1H, m), 2.02 (1H, m), 1.85 (1H, m), 1.28 (3H, s), 0.96 (3H, d, J=7.2 Hz), 0.90 (3H, d, J=6.3 Hz).

Example 42: Preparation of (10S)—O-{4-[2-[4-(4-fluorophenyl)piperazin-1-yl]-2-oxoethyl]phenyl}-dihydroartemisinin According to the preparation method of Example 33, the title compound was prepared by using the raw material 4-(2-methoxyphenyl) piperazine instead of pyrrolidine, as a white solid with a yield of 14.8%, mp: 92-94° C.
MS: (M+H) 581.8, (M+Na) 603.8;
$^1$H-NMR (300 MHz, DMSO-d$_6$): 7.17 (2H, d, J=8.4 Hz), 7.00 (4H, m), 6.98 (2H, d, J=8.4 Hz), 5.50 (1H, d, J=3.3 Hz), 5.42 (1H, s), 3.70 (2H, s), 3.61 (4H, m), 3.00 (4H, m), 2.57 (1H, m), 2.19 (1H, m), 2.02 (1H, m), 1.86 (1H, m), 1.28 (3H, s), 0.96 (3H, d, J=7.2 Hz), 0.90 (3H, d, J=6.3 Hz).

Example 43: Preparation of (10S)—O-{4-[2-(4-methyl-2-phenylpiperazin-1-yl)-2-oxoethyl]phenyl}-dihydroartemisinin According to the preparation method of Example 33, the title compound was prepared by using the raw material 1-methyl-3-phenylpiperazine instead of pyrrolidine, as a white solid with a yield of 6.3%, mp: 94-97° C.

MS: (M+H) 577.7, (M+Na) 599.6;

$^1$H-NMR (300 MHz, DMSO-$d_6$): 7.30 (5H m), 7.06 (4H, m), 5.53 (1H, d, J=3.3 Hz), 5.44 (1H, s), 3.89 (2H, s), 3.82 (1H, m), 2.61 (4H, m), 2.58 (1H, m), 2.19 (1H, m), 2.15 (3H, s), 2.02 (1H, m), 1.85 (1H, m), 1.28 (3H, s), 0.98 (3H, d, J=7.2 Hz), 0.91 (3H, d, J=6.3 Hz).

Example 44: Preparation of (10S)—O-{4-[2-[4-(pyridin-2-yl)piperazin-1-yl]-2-oxoethyl]phenyl}-dihydroartemisinin According to the preparation method of Example 33, the title compound was prepared by the raw material 4-(pyridin-2-yl)piperazine instead of pyrrolidine, as a while solid with a yield of 14.9%, mp: 116-118° C.

MS: (M+H) 564.8;

$^1$H-NMR (300 MHz, DMSO-$d_6$): 8.11 (1H, m), 7.56 (1H, m), 7.19 (2H, d, J=8.4 Hz), 6.99 (2H, d, J=8.4 Hz), 6.80 (1H, m), 6.65 (1H, m), 5.50 (1H, d, J=3.0 Hz), 5.42 (1H, s), 3.71 (2H, s), 3.58 (4H, m), 3.45 (4H, m), 2.57 (1H, m), 2.19 (1H, m), 2.02 (1H, m), 1.84 (1H, m), 1.28 (3H, s), 0.96 (3H, d, J=7.2 Hz), 0.90 (3H, d, J=6.0 Hz).

Example 45: Preparation of (10S)—O-{4-[2-[4-(pyrimidin-2-yl)piperazin-1-yl]-2-oxoethyl]phenyl}-dihydroartemisinin According to the preparation method of Example 33, the title compound was prepared by using the raw material 4-(pyrimidin-2-yl)piperazine instead of pyrrolidine, as a white solid with a yield of 17.2%, mp: 101-102° C.

MS: (M+H) 565.8, (M+Na) 587.8;

$^1$H-NMR (300 MHz, DMSO-$d_6$): 8.37 (2H, d, J=8.4 Hz), 7.19 (2H, d, J=8.4 Hz), 6.99 (2H, d, J=8.4 Hz), 6.80 (1H, m), 6.66 (1H, t), 5.50 (1H, d, J=3.0 Hz), 5.42 (1H, s), 3.71 (2H, s), 3.68 (4H, m), 3.57 (4H, m), 2.57 (1H, m), 2.19 (1H, m), 2.02 (1H, m), 1.84 (1H, m), 1.28 (3H, s), 0.96 (3H, d, J=7.2 Hz), (1.90 (3H, d, J=6.0 Hz).

Example 46: Preparation of (10S)—O-{4-[2-(4-cyclohexylpiperazin-1-yl)-2-oxoethyl]phenyl}-dihydroartemisinin According to the preparation method of Example 33, the title compound was prepared by using the raw material 4-cyclohexylpiperazine instead of pyrrolidine, as a white solid with a yield of 14.5%, mp: 89-92° C.

MS: (M+H) 569.7, (M+Na) 591.7;

$^1$H-NMR (300 MHz, DMSO-$d_6$): 7.15 (2H, d, J=8.7 Hz), 6.99 (2H, d, J=8.7 Hz), 5.50 (1H, d, J=3.0 Hz), 5.42 (1H, s), 3.62 (2H, s), 3.44 (4H, m), 2.58 (1H, m), 2.43 (4H, m), 2.19 (1H, m), 2.02 (1H, m), 1.84 (1H, m), 1.65 (3H, m), 1.40 (5H, m), 1.28 (3H, s), 1.19 (8H, m), 0.97 (3H, d, J=7.5 Hz), 0.91 (3H, d, J=6.3 Hz).

Example 47: Preparation of (10S)—O-[4-(2-phenylamino-2-oxoethyl)phenyl]-dihydroartemisinin Step A: Preparation of 2-(4-hydroxyphenyl)-N-phenylacetamide

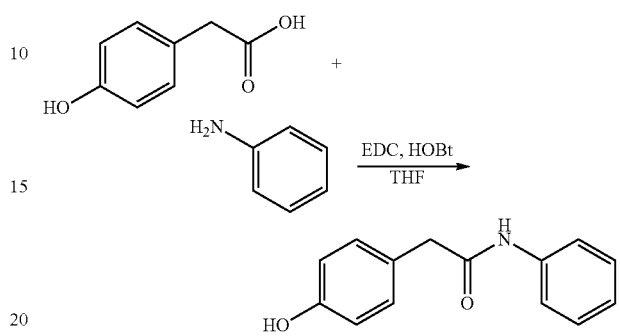

7.56 g (0.005 mol) (4-hydroxyphenyl)acetic acid, 0.68 g (0.005 mol) EDC and 0.96 g (0.005 mol) HOBt were dissolved in 20 mL refined THF. After the mixture was stirred for 10 min in an ice bath, 0.45 mL (0.005 mol) aniline was added thereto dropwise. The reaction was kept overnight at room temperature and monitored by TLC. After completion of the reaction, THF was evaporated off. The residue was dissolved in 20 mL CH$_2$Cl$_2$, and washed with a saturated aqueous sodium chloride solution (3×20 mL). The organic layer was dried over anhydrous sodium sulfate overnight, and then was separated by silica gel column chromatography (methylene dichloride:methanol (v/v)=50:1) to give a yellow powder with a yield of 78.3%.

Step B: Preparation of dihydroartemisinin-(10S)—O-trifluoroacetic ester

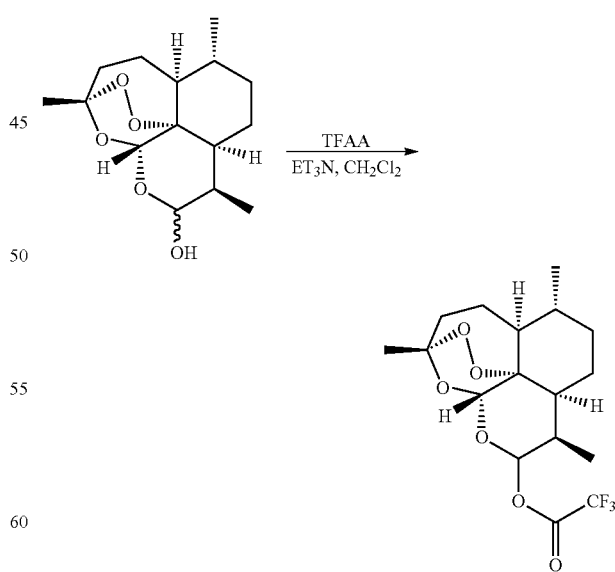

2.84 g (0.01 mol) DHA, 1.52 g (0.015 mol) triethylamine, and 50 mL refined CH$_2$Cl$_2$ were stirred for 30 min in an ice salt bath, and 3.15 g (0.015 mol) trifluoroacetic anhydride (TFAA) was added thereto dropwise. The reaction was stirred until the disappearance of the starting material dihydroartemisinin as monitored by TLC, which was ready for use without any treatment.

Step C: Preparation of (10S)—O-[4-(2-phenylamino-2-oxoethyl)phenyl]-dihydroartemisinin

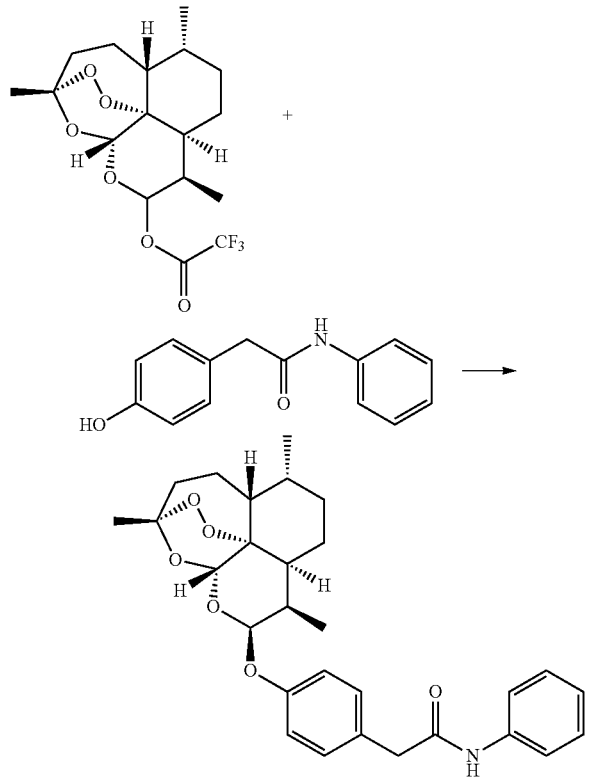

1.14 g (0.0005 mol) 2-(4-hydroxyphenyl)-N-phenylacetamide was added to the above prepared solution of the artemisinin active ester, and the mixture was stirred for 24 hr at room temperature. The resulting solution was washed with 5% sodium hydroxide aqueous solution (3×30 mL), 50 mL water and 50 mL of a saturated aqueous sodium chloride solution successively. The $CH_2Cl_2$ layer was dried over anhydrous sodium sulfate overnight. After filtration of the desiccant, the filtrate was concentrated under reduced pressure, and then was separated by silica gel column chromatography (methylene dichloride:acetone (v/v)=10-5:1) to give a white solid with a yield of 14.7%. mp: 172-173° C.

MS: (M+H) 494.6, (M+Na) 516.6;

$^1$H-NMR (300 MHz, DMSO-$d_6$): 10.09 (1H, s), 7.58 (2H, d, J=7.8 Hz), 7.30 (2H, d, J=8.4 Hz), 7.25 (2H, m), 7.03 (1H, m), 7.02 (2H, d, J=8.4 Hz), 5.50 (1H, d, J=3.0 Hz), 5.42 (1H, s), 3.57 (2H, s), 2.58 (1H, m), 2.19 (1H, m), 2.02 (1H, m), 1.84 (1H, m), 1.28 (3H, s), 0.97 (3H, d, J=7.2 Hz), 0.91 (3H, d, J=6.3 Hz).

Example 48: Preparation of (10S)—O-[4-[2-(benzylamino)-2-oxoethyl]phenyl]-dihydroartemisinin According to the preparation method of Example 48, the title compound was prepared by using the raw material benzylamine instead of aniline, as a white solid with a yield of 11.6%, mp: 81-82° C.

MS: (M+H) 508.6, (M+Na) 530.6;

$^1$H-NMR (300 MHz, DMSO-$d_6$): 8.47 (1H, t), 7.32 (2H, d, J=7.8 Hz), 7.25 (5H, m), 7.00 (2H, d, J=8.1 Hz), 5.50 (1H, d, J=3.0 Hz), 5.42 (1H, s), 4.26 (2H, d), 3.42 (2H, s), 2.58 (1H, m), 2.19 (1H, m), 2.02 (1H, m), 1.84 (1H, m), 1.28 (3H, s), 0.97 (3H, d, J=7.5 Hz), 0.91 (3H, d, J=6.3 Hz).

Pharmacology of the Present Compounds

In Vitro Anti-Rumor Activity Test

1) Cell Thawing

Cells were taken out carefully from liquid nitrogen (Frozen pipes), and the cell freezing medium was thawed rapidly in water bath at 37° C. in order to rapidly pass through the temperature range of 0 to 5° C. within which the cell is easily damaged. Cell suspension was sucked with pipette gun and put it into centrifugal tubes under sterile condition, then was centrifuged for 3 min at 1300 r/min. The supernatant was gently discarded, and then added with a fresh medium to pipette and mix the cells. Finally, the cells were transferred into culture flasks, and cultured in a carbon dioxide incubator. The medium was changed once after 24 h.

2) Cell Culture

Human leukemia cells (HL-60) were cultured in RPMI1640 medium containing 10% (v/v) fetal bovine serum, 100 U/mL penicillin and 100 μg/mL streptomycin. Murine leukemia cells (P388) and murine multidrug resistant leukemia cells (P388/Adr) were cultured in Eagle's minimum essential medium (MEM) containing 10% (v/v) fetal bovine serum, 100 U/mL penicillin and 100 μg/mL streptomycin. All of the above cell lines were incubated in 37° C. incubator with 5% carbon dioxide saturated humidity.

3) Cell Passage

After resuscitation, the cells were passed for 2-3 generations till they became stable, then they were used for the experiments. Each passage was based on the standard that all cells were spread over the bottoms of culture flasks.

4) Direct Cell Counting Method to Investigate Cell Growth Inhibitory Activity of Compounds Cell suspensions of a certain density (5×104 cells/mL) were plated at 24-well plate, 2 mL/well. Different concentration of drugs were added thereto, and incubated or some time. Then, cells were counted under the microscope. The ratio of total number of cells in test group to the total number of cells in control group is the cell growth inhibition rate under the concentration condition. The total number of cells in cell suspension, which were treated by drugs, could be counted by blood count board. Inhibition rate was calculated using the formula:

$$\text{Cell growth inhibition rate}(\%) = \left(1 - \frac{\text{The total number of cells in test group}}{\text{The total number of cells in control group}}\right) \times 100\%$$

According to cell growth inhibition rate of each concentration of drugs, half inhibitory concentration could be calculated. ($IG_{50}$ is the drug concentration, when cell growth inhibition rate was 50%.)

5) The Results of the Growth Inhibitory Activity of the Compounds on Human Leukemia Cells (HL-60) were Listed in Table 1.

TABLE 1

The IC$_{50}$ value list of the compounds on HL-60 cells

| Example No. | IG$_{50}$ (µmol/L) |
|---|---|
| Example 5 | 0.228 |
| Example 6 | 0.079 |
| Example 7 | 0.120 |
| Example 8 | 0.083 |
| Example 9 | 0.071 |
| Example 10 | 0.033 |
| Example 16 | 0.105 |
| Example 17 | 0.059 |

6) The Results of the Growth Inhibitory Activity of the Compounds on Murine Leukemia Cells (P388) and Murine Multidrug Resistant Leukemia Cells (P388/Adr) were Listed in Table 2.

TABLE 2

The IC$_{50}$ value list of the compounds on P388 and P388/Adr cells

| | IG$_{50}$ (µM) | |
|---|---|---|
| Example No. | P388 | P388/Adr |
| Example 5 | 0.880 | 0.804 |
| Example 10 | 0.070 | 0.088 |
| Example 24 | 0.299 | 0.918 |
| Example 25 | 0.152 | 0.223 |
| Example 26 | 0.145 | 0.153 |

7) The Results of the Growth Inhibitory Activity of the Compounds on Human Breast Cancer Cells (MCF-7) and Human Multidrug Resistant Breast Cancer Cells (MCF-7/Adr) were Listed in Table 3.

TABLE 3

The IC$_{50}$ value list of the compounds on MCF-7 and MCF-7/Adr cells

| | IG$_{50}$ (µM) | |
|---|---|---|
| Example No. | MCF-7 | MCF-7/Adr |
| Example 2 | 0.211 | 0.631 |
| Example 3 | 1.32 | 0.718 |
| Example 4 | 1.62 | 0.476 |
| Example 11 | 0.475 | 0.456 |
| Example 12 | 1.05 | 0.190 |
| Example 13 | 0.267 | 0.330 |
| Example 14 | 1.28 | 1.38 |
| Example 15 | 0.443 | 1.66 |
| Example 18 | 0.690 | 0.355 |
| Example 19 | 1.19 | 1.09 |
| Example 20 | 0.123 | |
| Example 21 | 0.241 | |
| Example 22 | 0.00607 | |
| Example 23 | 0.586 | |
| Example 27 | 0.322 | |
| Example 28 | 0.0911 | |
| Example 29 | 0.0156 | |
| Example 30 | 0.263 | |
| Example 31 | 0.0630 | |
| Example 32 | 0.408 | |
| Example 33 | 3.23 | 0.122 |
| Example 34 | 7.58 | 0.239 |
| Example 35 | 1.70 | 0.0624 |
| Example 36 | 0.549 | 0.104 |
| Example 37 | 1.25 | |
| Example 38 | 0.516 | 0.360 |
| Example 39 | 1.15 | 0.0229 |
| Example 40 | 2.66 | 0.0791 |
| Example 41 | 0.790 | 0.0298 |
| Example 42 | 1.09 | 0.0112 |
| Example 43 | 2.29 | 1.06 |
| Example 44 | 1.49 | 0.180 |
| Example 45 | 1.49 | 0.110 |
| Example 46 | 1.12 | 0.0980 |
| Example 47 | 1.55 | 0.00966 |
| Example 48 | 1.40 | |

What is claimed is:

1. A nitrogen-containing heterocycle substituted dihydroartemisinin derivative of formula I:

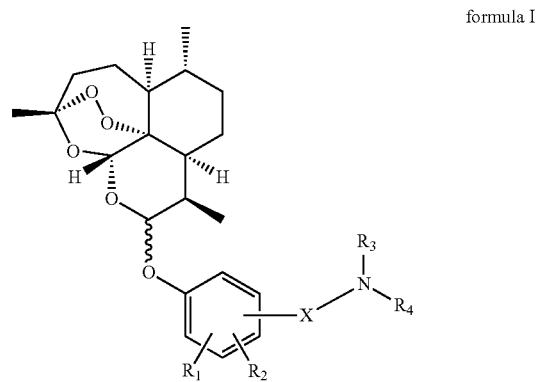

formula I wherein,

X is —(CH$_2$)$_n$—,

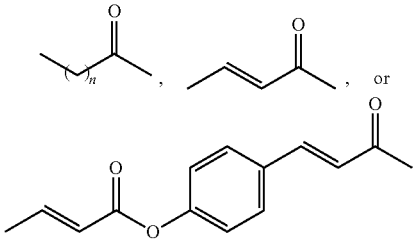

wherein n is independently an integer of from 1 to 3;

Y is CH, N, or O;

R$_3$ and R$_4$, together with the nitrogen atom to which they attached, form a 5-membered saturated or unsaturated heterocyclic group, which may, in addition to the nitrogen atom connected by R$_3$ and R$_4$, contain 0 to 2 heteroatoms selected from N, O and S, and may be optionally substituted with 1 to 3 same or different substituents selected from R$_5$;

and

R$_1$-R$_2$ and R$_5$ are independently selected from hydrogen, halogen, trifluoromethyl, trifluoromethoxy, hydroxyl, carboxyl, nitro, cyano, (C$_1$-C$_4$) alkyl, or (C$_1$-C$_4$) alkoxy.

2. The nitrogen-containing heterocyclic ring-substituted dihydroartemisinin derivative according to claim 1, wherein in the formula I, X is —(CH$_2$)$_n$—,

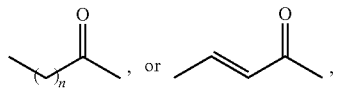

and n is independently an integer of from 1 to 3;

R$_3$ and R$_4$, together with the nitrogen atom to which they attached, form a 5-membered saturated and unsaturated heterocyclic group, which may, in addition to the nitrogen atom connected by R$_5$ and R$_6$, contain 0 to 2 heteroatoms selected from N, O and S, and may be optionally substituted with 1 to 3 same or different substituents selected from R$_5$; and R$_5$ is independently selected from hydrogen, halogen, trifluoromethyl, trifluoromethoxy, hydroxyl, carboxyl, nitro, cyano, (C$_1$-C$_4$) alkyl, or (C$_1$-C$_4$) alkoxy.

3. A pharmaceutical composition comprising the nitrogen-containing heterocyclic ring-substituted dihydroartemisinin derivative according to claim 1, or its optical isomer, and a pharmaceutically acceptable excipient.

4. A method of inducing apoptosis, comprising contacting a cell with an effective amount of the nitrogen-containing heterocyclic ring-substituted dihydroartemisinin derivative according to claim 1.

5. A method of treating cancer, comprising administering to a subject in need of such treatment, an effective amount of the nitrogen-containing heterocyclic ring-substituted dihydroartemisinin derivative according to claim 1.

6. A nitrogen-containing heterocycle substituted dihydroartemisinin derivative of formula II:

formula II

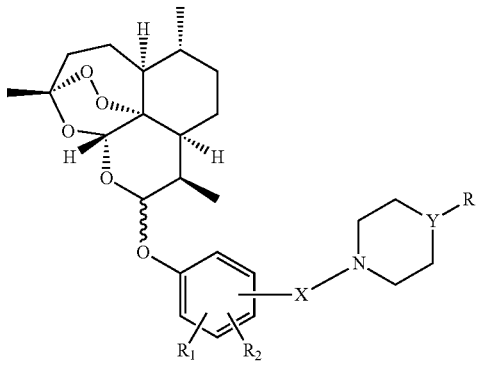

wherein,
X is

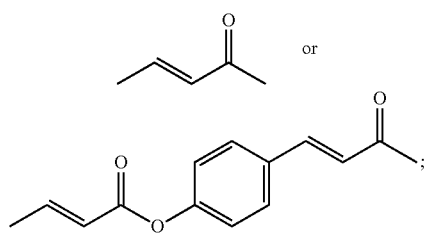

Y is CH, N, or O;
R is hydrogen, C$_1$-C$_{10}$ alkyl, a C$_3$-C$_7$ cycloalkyl group containing 1 to 2 heteroatoms selected from N, O and S, Ar,

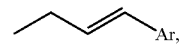

wherein Ar is phenyl optionally substituted with 1 to 5 same or different substituents selected from R$_6$, or 5-membered heteroaryl optionally substituted with 1 to 5 same or different substituents selected from R$_7$, said heteroaryl contain 1 to 3 heteroatoms selected from N; and R$_1$-R$_2$ and R$_6$-R$_7$ are independently selected from hydrogen, halogen, trifluoromethyl, trifluoromethoxy, hydroxyl, carboxyl, nitro, cyano, (C$_1$-C$_4$) alkyl, or (C$_1$-C$_4$) alkoxy.

7. A nitrogen-containing heterocycle substituted dihydroartemisinin derivative of formula II:

formula II

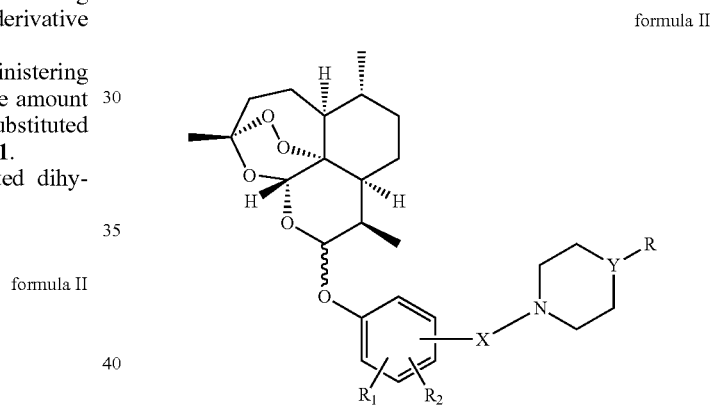

wherein, X is

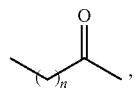

and n is 1;
Y is CH, or N;
R is C$_1$-C$_4$ alkyl, a C$_3$-C$_7$ cycloalkyl group containing 1 to 2 heteroatoms selected from N, O and S, Ar,

wherein Ar is phenyl optionally substituted with 1 to 5 same or different substituents selected from R$_6$, or 5-membered heteroaryl optionally substituted with 1 to 5 same or different substituents selected from R$_7$, said heteroaryl contain 1 to 3 heteroatom selected from N; and R$_1$-R$_2$ and R$_6$-R$_7$ are independently selected from hydrogen, halogen, trifluoromethyl, (C$_1$-C$_4$) alkyl, or (C$_1$-C$_4$) alkoxy.

8. A nitrogen-containing heterocycle substituted dihydroartemisinin derivative selected from:
- (10S)—O-[4-((pyrrolidin-1-yl)methyl)phenyl]-dihydroartemisinin
- (10S)—O-[4-((imidazol-1-yl)methy)phenyl]-dihydroartemisinin
- (10S)—O-[4-((1,2,3-triazol-1-yl)methyl)phenyl]-dihydroartemisinin
- (10S)—O-[4-((1,2,4-triazol-1-yl)methyl)phenyl]-dihydroartemisinin
- (10S)—O-[4-((piperidin-1-yl)methyl)phenyl]-dihydroartemisinin
- (10S)—O-[4-[(4-(piperidinyl)piperidin-1-yl)methyl]phenyl]-dihydroartemisinin
- (10S)—O-[4-((4-methylpiperazin-1-yl)methyl)phenyl]-dihydroartemisinin
- (10S)—O-[4-((4-ethylpiperazin-1-yl)methyl)phenyl]-dihydroartemisinin
- (10S)—O-[4-((4-isopropylpiperazin-1-yl)methyl)phenyl]-dihydroartemisinin
- (10S)—O-[4-((4-phenylpiperazin-1-yl)methyl)phenyl]-dihydroartemisinin
- 10-O-[4-[(4-(2-methoxyphenyl)piperazin-1-yl)methyl]phenyl]-(10S)-dihydroartemisinin
- 10-O-[4-[(4-(3-trifluoromethylphenyl)piperazin-1-yl)methyl]phenyl]-(10S)-dihydroartemisinin
- 10-O-[4-[(4-(4-flurophenyl)piperazin-1-yl)methyl]phenyl]-(10S)-dihydroartemisinin
- 10-O-[4-[(4-(2-pyridyl)piperazin-1-yl)methyl]phenyl]-(10S)-dihydroartemisinin
- 10-O-[4-[(4-(2-pyrimidinyl)piperazin-1-yl)methyl]phenyl]-(10S)-dihydroartemisinin
- 10-O-[4-[(4-benzylpiperazin-1-yl)methyl]phenyl]-(10S)-dihydroartemisinin
- 10-O-[4-[(4-cinnamylpiperazin-1-yl)methyl]phenyl]-(10S)-dihydroartemisinin
- 10-O-[3-[(4-phenylpiperazin-1-yl)methyl]phenyl]-(10S)-dihydroartemisinin
- 10-O-[3-[(4-benzylpiperazin-1-yl)methyl]phenyl]-(10S)-dihydroartemisinin
- (10S)—O-{4-[3-oxo-3-(pyrrolidin-1-yl)-1-(E)-propen-1-yl]phenyl}-dihydroartemisinin
- (10S)—O-{4-[3-oxo-3-(morpholin-4-yl)-1-(E)-propen-1-yl]phenyl}-dihydroartemisinin
- (10S)—O-{4-[3-oxo-3-(piperidin-1-yl)-1-(E)-propen-1-yl]phenyl}-dihydroartemisinin
- (10S)—O-{4-[3-oxo-3-(4-(piperidin-1-yl)piperidine-1-(E)-propen-1-yl]phenyl}-dihydroartemisinin
- (10S)—O-{4-[3-oxo-3-(4-methylpiperazin-1-yl)-1-(E)-propen-1-yl]phenyl}-dihydroartemisinin
- (10S)—O-{4-[3-oxo-3-(4-ethylpiperazin-1-yl)-1-(E)-propen-1-yl]phenyl}-dihydroartemisinin
- (10S)—O-{4-[3-oxo-3-(4-phenylpiperazin-1-yl)-1-(E)-propen-1-yl]phenyl}-dihydroartemisinin
- (10S)—O-{4-[3-oxo-3-(4-(2-methoxyphenyl)piperazin-1-yl)-1-(E)-propen-1-yl]phenyl}-dihydroartemisinin
- (10S)—O-{4-[3-oxo-3-(4-(3-trifluoromethylphenyl)piperazin-1-yl)-1-(E)-propen-1-yl]phenyl}-dihydroartemisinin
- (10S)—O-{4-[3-oxo-3-(4-benzylpiperazin-1-yl)-1-(E)-propen-1-yl]phenyl}-dihydroartemisinin
- (10S)—O-{4-[3-oxo-3-(4-(2-pyridyl)piperazin-1-yl)-1-(E)-propen-1-yl]phenyl}-dihydroartemisinin
- 4-[(10S)-dihydroartemisinin-10-O-yl]phenyl-acrylic acid-4-[3-oxo-3-(piperidin-1-yl)-1-(E)-propen-1-yl]phenyl ester
- 4-[(10S)-dihydroartemisinin-10-O-yl]phenyl-acrylic acid-4-[3-oxo-3-(4-(2-pyrimidinyl)piperazin-1-yl)-1-(E)-propen-1-yl]phenyl ester
- (10S)—O-{4-[2-(pyrrolidin-1-yl)-2-oxoethyl]phenyl}-dihydroartemisinin
- (10S)—O-{4-[2-(morpholin-4-yl)-2-oxoethyl]phenyl}-dihydroartemisinin
- (10S)—O-{4-[2-(piperidin-1-yl)-2-oxoethyl]phenyl}-dihydroartemisinin
- (10S)—O-{4-[2-(4-methylpiperidin-1-yl)-2-oxoethyl]phenyl}-dihydroartemisinin
- (10S)—O-{4-[2-(2-methylpiperidin-1-yl)-2-oxoethyl]phenyl}-dihydroartemisinin
- (10S)—O-{4-[2-(3,5-dimethylpiperidin-1-yl)-2-oxoethyl]phenyl}-dihydroartemisinin
- (10S)—O-{4-[2-[4-(piperidin-1-yl)piperidin-1-yl]-2-oxoethyl]phenyl}-dihydroartemisinin
- (10S)—O-{4-[2-(4-phenylpiperazin-1-yl)-2-oxoethyl]phenyl}-dihydroartemisinin
- (10S)—O-{4-[2-[4-(2-methoxyphenyl)piperazin-1-yl]-2-oxoethyl]phenyl}-dihydroartemisinin
- (10S)—O-{4-[2-[4-(4-fluorophenyl)piperazin-1-yl]-2-oxoethyl]phenyl}-dihydroartemisinin
- (10S)—O-{4-[2-[4-(pyridin-2-yl)piperazin-1-yl]-2-oxoethyl]phenyl}-dihydroartemisinin
- (10S)—O-{4-[2-[4-(pyrimidin-2-yl)piperazin-1-yl]-2-oxoethyl]phenyl}-dihydroartemisinin
- (10S)—O-{4-[2-(4-cyclohexylpiperazin-1-yl)-2-oxoethyl]phenyl}-dihydroartemisinin
- (10S)—O-[4-(2-phenylamino-2-oxoethyl)phenyl]-dihydroartemisinin or
- (10S)—O-[4-[2-(benzylamino)-2-oxoethyl]phenyl]-dihydroartemisinin.

9. A pharmaceutical composition comprising the nitrogen-containing heterocyclic ring-substituted dihydroartemisinin derivative according to claim 6, or its optical isomer, and a pharmaceutically acceptable excipient.

10. A pharmaceutical composition comprising the nitrogen-containing heterocyclic ring-substituted dihydroartemisinin derivative according to claim 7, or its optical isomer, and a pharmaceutically acceptable excipient.

11. A pharmaceutical composition comprising the nitrogen-containing heterocyclic ring-substituted dihydroartemisinin derivative according to claim 8, or its optical isomer, and a pharmaceutically acceptable excipient.

12. A method of inducing apoptosis, comprising contacting a cell with an effective amount of the nitrogen-containing heterocyclic ring-substituted dihydroartemisinin derivative according to claim 6.

13. A method of treating cancers, comprising administering to a subject in need of such treatment, an effective amount of the nitrogen-containing heterocyclic ring-substituted dihydroarternisinin derivative according to claim 6.

14. A method of inducing apoptosis, comprising contacting a cell with an effective amount of the nitrogen-containing heterocyclic ring-substituted dihydroartemisinin derivative according to claim 7.

15. A method of inducing apoptosis, comprising contacting a cell with an effective amount of the nitrogen-containing heterocyclic ring-substituted dihydroartemisinin derivative according to claim 7.

16. A method of treating cancers, comprising administering to a subject in need of such treatment, an effective amount of the nitrogen-containing heterocyclic ring-substituted dihydroartemisinin derivative according to claim 8.

17. A method of inducing apoptosis, comprising contacting a cell with an effective amount of the nitrogen-containing heterocyclic ring-substituted dihydroartemisinin derivative according to claim 8.

* * * * *